(12) United States Patent
Bergh et al.

(10) Patent No.: US 8,592,220 B2
(45) Date of Patent: *Nov. 26, 2013

(54) HIGH PRESSURE PARALLEL FIXED BED REACTOR AND METHOD

(75) Inventors: H. Sam Bergh, San Mateo, CA (US); Jason Wells, San Francisco, CA (US); Victor Wong, San Jose, CA (US); John Gallipeo, Morgan Hill, CA (US); Lynn Van Erden, Pollock Pines, CA (US); Anthony F. Volpe, Santa Clara, CA (US); Jeffrey Maag, Belmont, CA (US)

(73) Assignee: Intermolecular, Inc., San Jose, CA (US)

( * ) Notice: Subject to any disclaimer, the term of this patent is extended or adjusted under 35 U.S.C. 154(b) by 585 days.

This patent is subject to a terminal disclaimer.

(21) Appl. No.: 12/447,143

(22) PCT Filed: Oct. 26, 2007

(86) PCT No.: PCT/US2007/082685
§ 371 (c)(1),
(2), (4) Date: Feb. 15, 2010

(87) PCT Pub. No.: WO2008/052168
PCT Pub. Date: May 2, 2008

(65) Prior Publication Data
US 2010/0144539 A1    Jun. 10, 2010

Related U.S. Application Data

(60) Provisional application No. 60/854,760, filed on Oct. 26, 2006.

(51) Int. Cl.
*G01N 1/10* (2006.01)

(52) U.S. Cl.
USPC .............. 436/180; 422/89; 422/500; 422/501

(58) Field of Classification Search
USPC ............................ 422/500, 501, 89; 436/180
See application file for complete search history.

(56) References Cited

U.S. PATENT DOCUMENTS

| | | | |
|---|---|---|---|
| 3,431,077 A | 3/1969 | Danforth |
| 3,536,452 A | 10/1970 | Norton |
| 3,760,831 A | 9/1973 | Colvin |
| 4,061,870 A | 12/1977 | Mizushina |
| 4,099,923 A | 7/1978 | Milberger |
| 4,670,404 A | 6/1987 | Swift |
| 4,705,669 A | 11/1987 | Tsuji |
| 4,895,706 A | 1/1990 | Root |
| 4,923,306 A | 5/1990 | Fauske |
| 4,996,387 A | 2/1991 | Gerhold |
| 5,035,866 A | 7/1991 | Wannlund |
| 5,089,232 A | 2/1992 | May |
| 5,204,270 A | 4/1993 | LaCount |
| 5,229,075 A | 7/1993 | Fauske |
| 5,246,665 A | 9/1993 | Tyranski |
| 5,252,294 A | 10/1993 | Kroy |
| 5,304,354 A | 4/1994 | Finley |
| 5,324,483 A | 6/1994 | Cody |
| 5,340,475 A | 8/1994 | Cortes |
| 5,417,938 A | 5/1995 | Shelden |
| 5,534,328 A | 7/1996 | Ashmead |
| 5,547,282 A | 8/1996 | Pinhack |
| 5,580,523 A | 12/1996 | Bard |
| 5,587,128 A | 12/1996 | Wilding |
| 5,589,136 A | 12/1996 | Northrup |
| 5,593,642 A | 1/1997 | DeWitt |
| 5,595,712 A | 1/1997 | Harbster |
| 5,603,351 A | 2/1997 | Cherukuri |
| 5,611,214 A | 3/1997 | Wegeng |
| 5,639,423 A | 6/1997 | Northrup |
| 5,658,537 A | 8/1997 | Dugan |
| 5,667,009 A | 9/1997 | Moore |
| 5,690,763 A | 11/1997 | Ashmead |
| 5,710,381 A | 1/1998 | Atwood |
| 5,753,185 A | 5/1998 | Mathews |
| 5,780,748 A | 7/1998 | Barth |
| 5,811,062 A | 9/1998 | Wegeng |
| 5,833,926 A | 11/1998 | Wurzel |
| 5,842,787 A | 12/1998 | Kopf-Sill |

(Continued)

FOREIGN PATENT DOCUMENTS

| DE | 234941 A1 | 4/1986 |
|---|---|---|
| EP | 0796654 | 9/1997 |

(Continued)

OTHER PUBLICATIONS

Burns, "Development of a Microreactor for Chemical Production", Process Miniaturization: 2nd Int'l Conference on Microreaction Technology, Mar. 9-12, 1998, New Orleans, LA, pp. 39-44.

(Continued)

*Primary Examiner* — Natalia Levkovich

(57) ABSTRACT

The present invention discloses an apparatus and method for rapid analysis of members of a combinatorial library. The apparatus includes a plurality of reactor vessels for containing individual library members, a fluid handling system that apportions a test fluid about equally between each of the vessels and a housing for enclosing the reactor vessels, the housing defining a pressure chamber, wherein the housing is configured to sustain a pressure substantially above atmospheric pressure. This allows for simultaneous screening of library members at high pressure by providing a small pressure differential on reactor components. The disclosed apparatus is especially useful for screening library members based on their ability to catalyze the conversion of fluid reactants.

28 Claims, 14 Drawing Sheets

(56) References Cited

U.S. PATENT DOCUMENTS

| | | | |
|---|---|---|---|
| 5,843,385 | A | 12/1998 | Dugan |
| 5,846,396 | A | 12/1998 | Zanzucchi |
| 5,863,801 | A | 1/1999 | Southgate |
| 5,866,342 | A | 2/1999 | Antonenko |
| 5,922,286 | A | 7/1999 | Girard |
| 6,004,515 | A | 12/1999 | Parce |
| 6,063,633 | A | 5/2000 | Willson, III |
| 6,067,864 | A | 5/2000 | Peterson |
| 6,090,251 | A | 7/2000 | Sundberg |
| 6,132,686 | A | 10/2000 | Gallup |
| 6,149,882 | A | 11/2000 | Guan |
| 6,157,009 | A | 12/2000 | Fauske |
| 6,175,409 | B1 | 1/2001 | Nielsen |
| 6,267,858 | B1 | 7/2001 | Parce |
| 6,306,658 | B1 | 10/2001 | Turner |
| 6,406,632 | B1 | 6/2002 | Safir |
| 6,447,727 | B1 | 9/2002 | Parce |
| 6,489,168 | B1 | 12/2002 | Wang |
| 6,556,940 | B1 | 4/2003 | Tretiakov |
| 6,576,197 | B1 | 6/2003 | Windhab |
| 6,576,470 | B1 | 6/2003 | Windhab |
| 6,616,909 | B1 | 9/2003 | Tonkovich |
| 6,667,009 | B1 | 12/2003 | Desrosiers |
| 6,680,044 | B1 | 1/2004 | Tonkovich |
| 6,691,999 | B2 | 2/2004 | Gunshera |
| 6,701,774 | B2 | 3/2004 | Srinivasan |
| 6,737,026 | B1 | 5/2004 | Bergh |
| 6,818,183 | B2 | 11/2004 | Hajduk |
| 6,828,096 | B1 | 12/2004 | Boussie |
| 6,869,799 | B1 | 3/2005 | Guan |
| 6,910,503 | B2 | 6/2005 | Schick |
| 7,021,820 | B2 | 4/2006 | Chippett |
| 7,122,156 | B2 | 10/2006 | Bergh |
| 7,150,994 | B2 | 12/2006 | Bergh |
| 7,172,732 | B2 | 2/2007 | Van Erden |
| 7,241,424 | B2 | 7/2007 | Guan |
| 2002/0042140 | A1 | 4/2002 | Hagemeyer |
| 2002/0048536 | A1* | 4/2002 | Bergh et al. .................. 422/130 |
| 2002/0085446 | A1 | 7/2002 | Van Den Brink |
| 2003/0190260 | A1 | 10/2003 | Wheeler |
| 2004/0141893 | A1 | 7/2004 | Martin |
| 2005/0009175 | A1 | 1/2005 | Bergh |
| 2005/0175519 | A1 | 8/2005 | Rogers, Jr. |
| 2005/0232074 | A1 | 10/2005 | Higashihara |

FOREIGN PATENT DOCUMENTS

| | | |
|---|---|---|
| EP | 1113869 B1 | 1/2005 |
| GB | 967261 | 8/1964 |
| WO | 9615576 | 5/1996 |

OTHER PUBLICATIONS

Franz, "New Operating Regimes and Applications Feasible with Microreactors", MIT, 1997, pp. 33-38.
Greenway, "The Use of Novel Microreactor for High Throughput Continuous Flow Organic Synthesis", Sensors and Actuators B, vol. 63, 2000, pp. 153-158.
Haswell, "The Application of Micro Reactors to Synthetic Chemistry", Chem. Commun., 2001, pp. 391-398.
Jackel, "Microtechnology: Application Opportunities in the Chemical Industry", DECHEMA Monographs, vol. 132, 1996, pp. 29-50.
Johansson, "Nanofabrication of Model Catalysts and Simulations of Their Reaction Kinetics", J. Vac. Sci. Technol. A, vol. 17, No. 1, Jan./Feb. 1999, pp. 297-302.
Klein, "Combinatorial Material Libraries on the Microgram Scale with an Example of Hydrothermal Synthesis", Angew. Chem. Int. Ed., vol. 37, No. 24, 1998, pp. 3369-3372.
Lowe, "Microreactor Concepts for Heterogeneous Gas Phase Reactions", Process Miniaturization: 2nd Int'l. Conference on Microreaction Technology, Mar. 9-12, 1998, New Orleans, LA, pp. 63-73.
Matlosz, "Microsectioned Electrochemical Reactors for Selective Partial oxidation", Process Miniaturization: 2nd Int'l. Conference on Microreaction Technology, Mar. 9-12, 1998, New Orleans, LA, pp. 54-59.
Perez-Ramirez, "The Six-Flow Reactor Technology: A Review on Fast Catalysis Screening and Kinetic Studies", Catalysis Today, vol. 60, 2000, pp. 93-109.
Sie, "Miniaturization of Hydroprocessing Catalyst Testing Systems: Theory and Practice", AlChE Journal, vol. 42, No. 12, Dec. 1996, pp. 3498-3507.
Srinivasan, "Micromachined Reactors for Catalytic Partial Oxidation Reactions", AlChE Journal, vol. 43, No. 11, Nov. 1997, pp. 3059-3069.
Tonkovich, "The Catalytic Partial Oxidation of Methane in a Microchannel Chemical Reactor", Process miniaturization: 2nd Int'l. Conference on Microreaction Technology, Mar. 9-12, 1998, New Orleans, LA, pp. 45-53.
Weissmeier, "Strategy for the Development of Micro Channel Reactors for Heterogenously Catalyzed Reactions", in Ehrfeld, Rinard, Wegner (Eds.) Process Miniaturization: 2nd International Conference on Microreaction Technology, IMRET 2, Topical Conference Preprints, pp. 24-32, AlChE, New Orleans (1998).
Zech, "Simultaneous Screening of Catalysts in Microchannels: Methodology and Experimental Setup" Ehrfeld and Wolfgang (Eds.), Springer-Verlag, Berlin, Germany, Proceedings of the Int'l. Conference on Microreaction Technology, 1999, pp. 260-266.
Zieren, "Time-Resolved Calorimetry in a New Type of Micro Fluid Reactor Using Specially Separated Thin-Film Themnoppiles and FIA-Technique", Process Miniaturization: 2nd Int'l Conference on Microreaction Technology, Mar. 9-12, 1998, New Orleans, LA, pp. 154-163.
Dyer, "Scale-Up of a Vilsmeier Formylation Reaction: Use of HEL Auto-MATE and Simulation Techniques for Rapid and Safe Transfer to Pilot Plant from Laboratory", Organic Process Research & Development, 2002, pp. 311-316, vol. 6 No. 3.
"Parr Calorimetry Methods and Modes", http://www.parrinst.com/default.cfm?page_ID=183, May 22, 2008, 2 pgs.
"Parr Calorimeter Selection", http://www.parrinst.com/default.cfm?page_ID=2-5, May 22, 2008, 6 pgs.
":reactor systems Parallel Process Optimisation", http://helgroup.com/home/ractor-systems/parallelprocessopt.html?subpage+3; Oct. 2, 2008, 2 pgs.
Simms, "Rapid Process Development and Scale-Up Using a Multiple Reactor System", Organic Process Research & Development, 2000, 9 pgs.
Singh, Parallel Synthesis of High Pressure Reactions—including catalyst development, date unknown, 9 pgs.
Steininger, "Four-Reactor Apparatus for Chromatographic Studies of Catalysts and Sorbents", Journal of Chromatography, 1982, 279-284, 243, Elsevier Scientific publishing Company, Amsterdam, Netherlands.
Wingaarden (Ed.), Industrial Catalysis-Optimizing Catalysts and Processes, 1998, Wiley-VCH Verlag GmbH, Weinheim, 99 pgs.

* cited by examiner

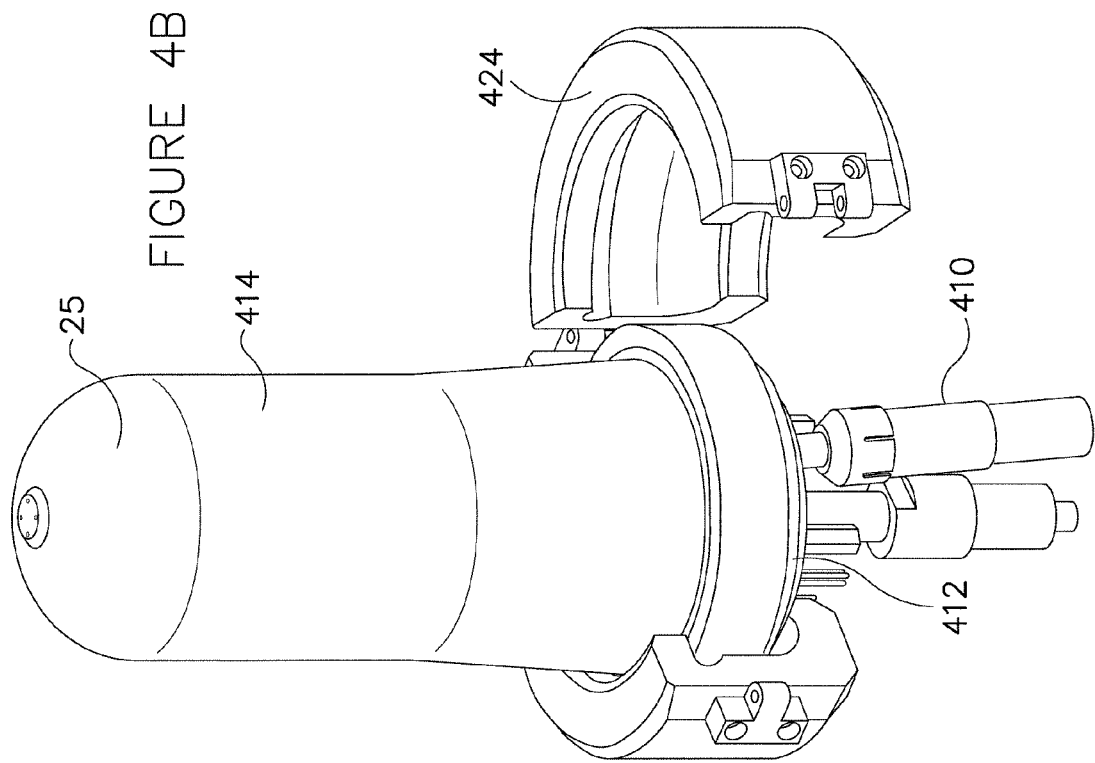
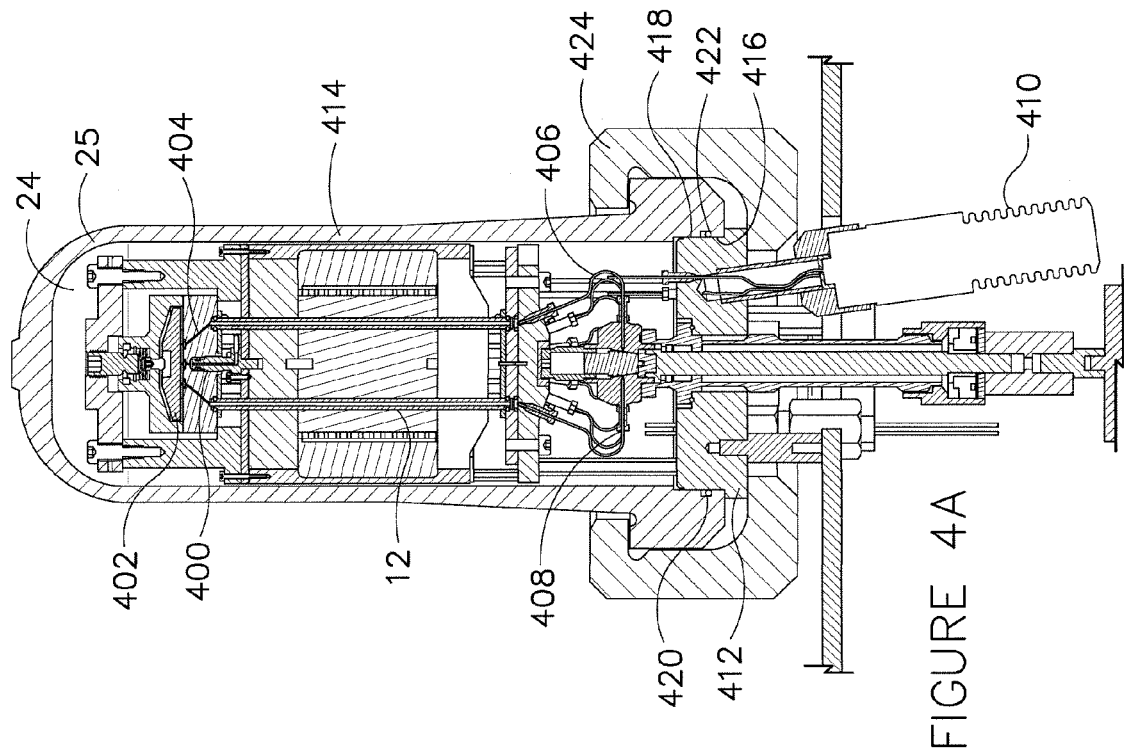

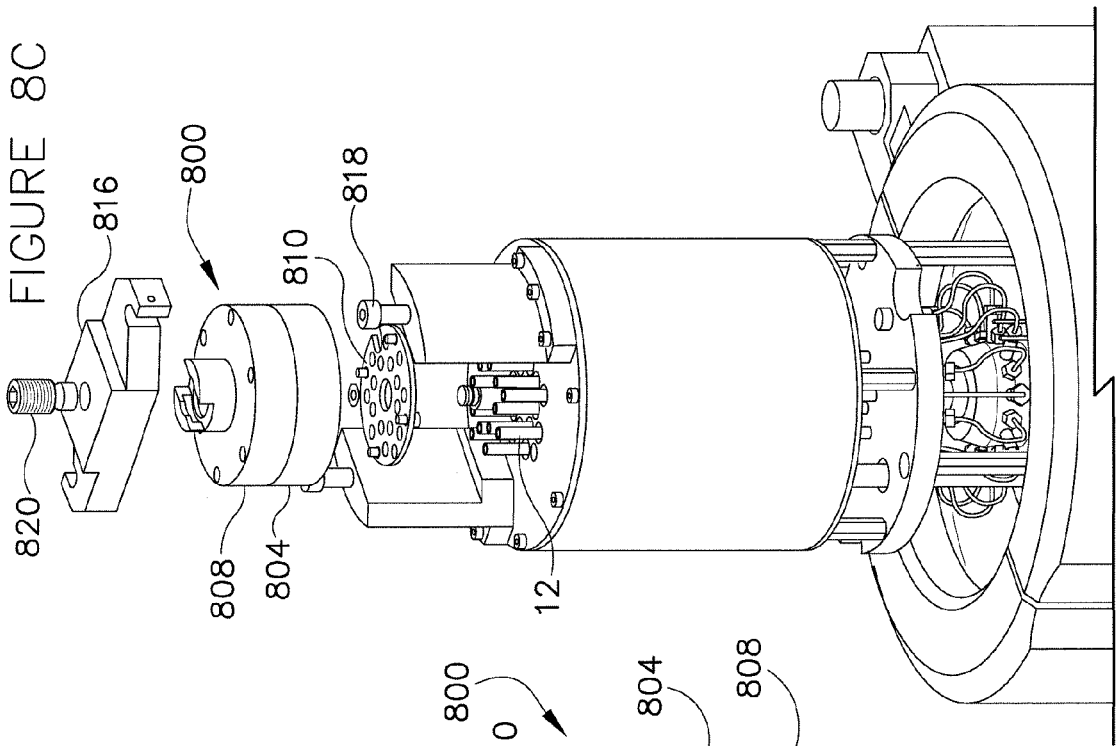
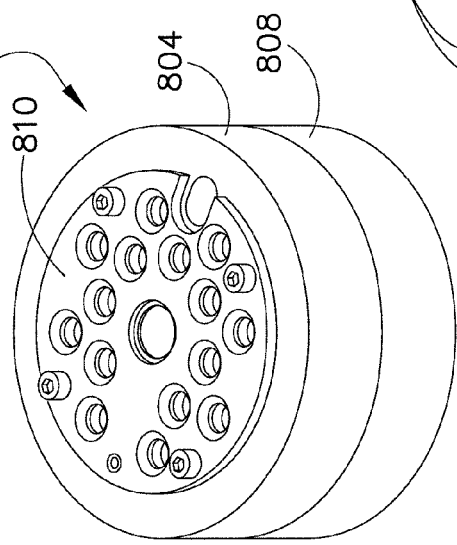
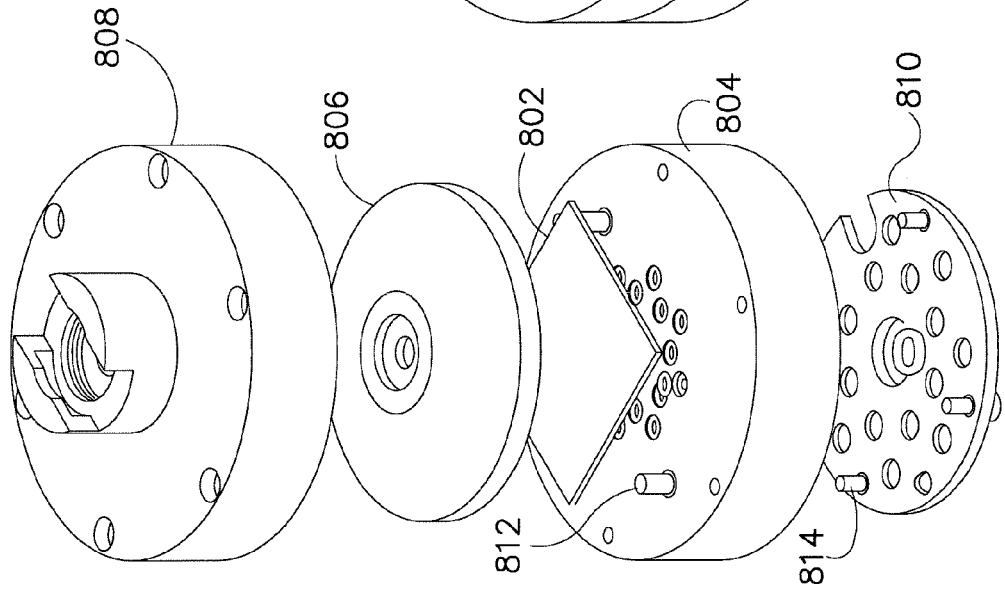

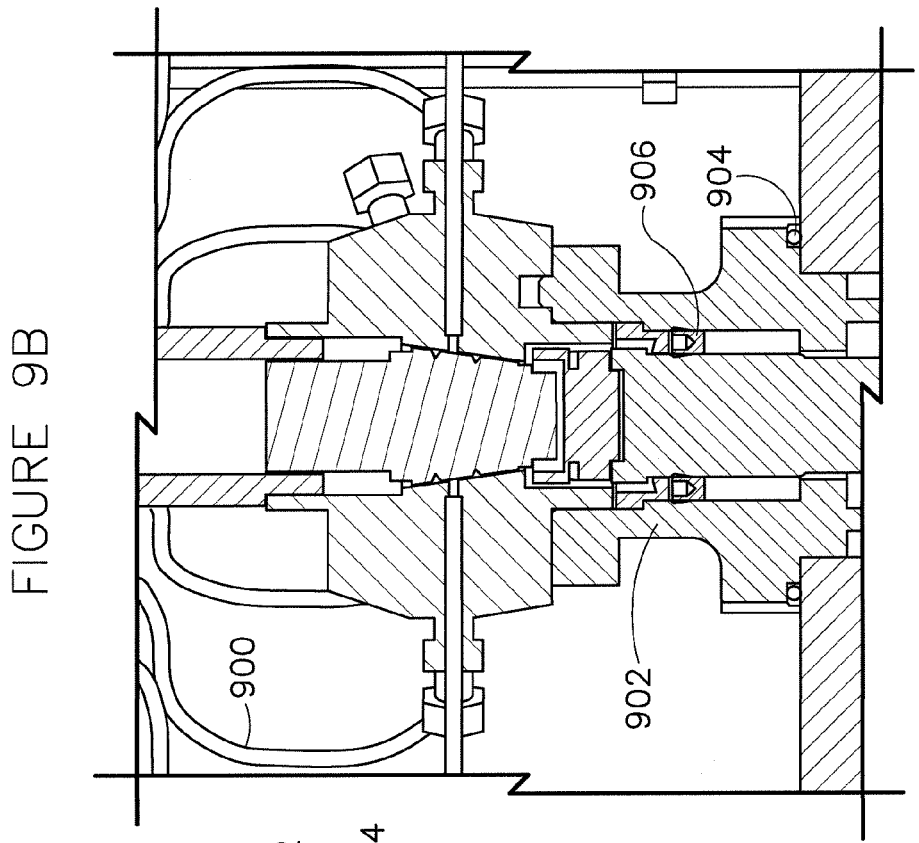
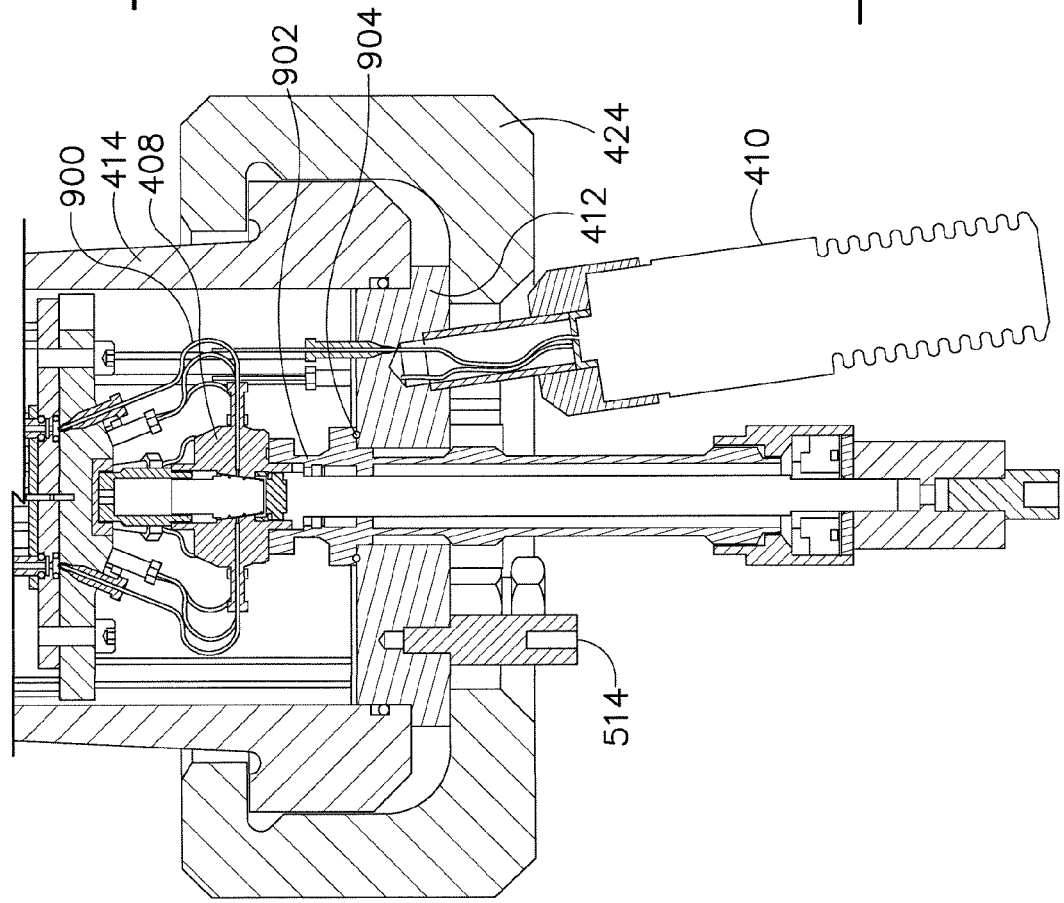

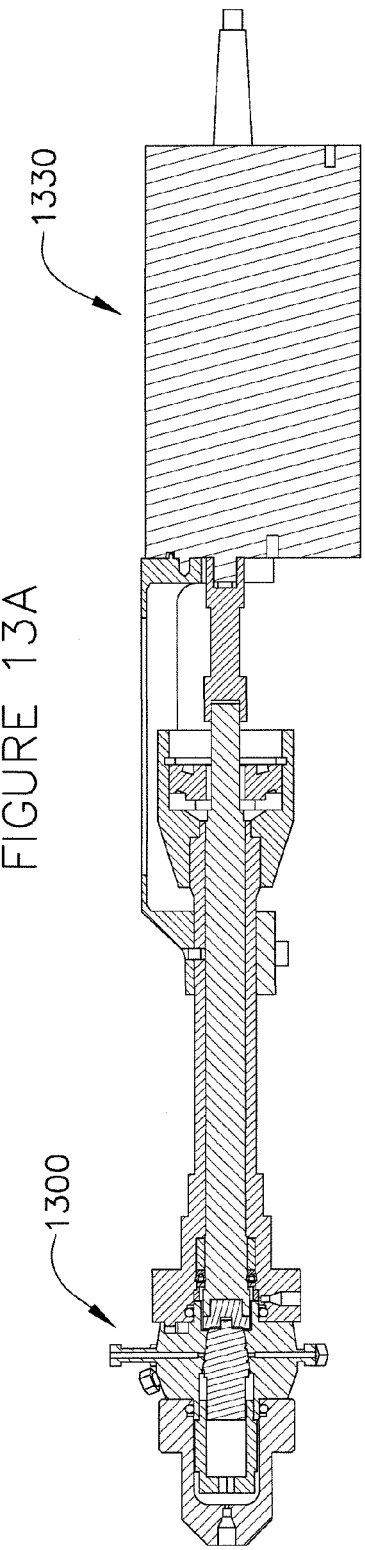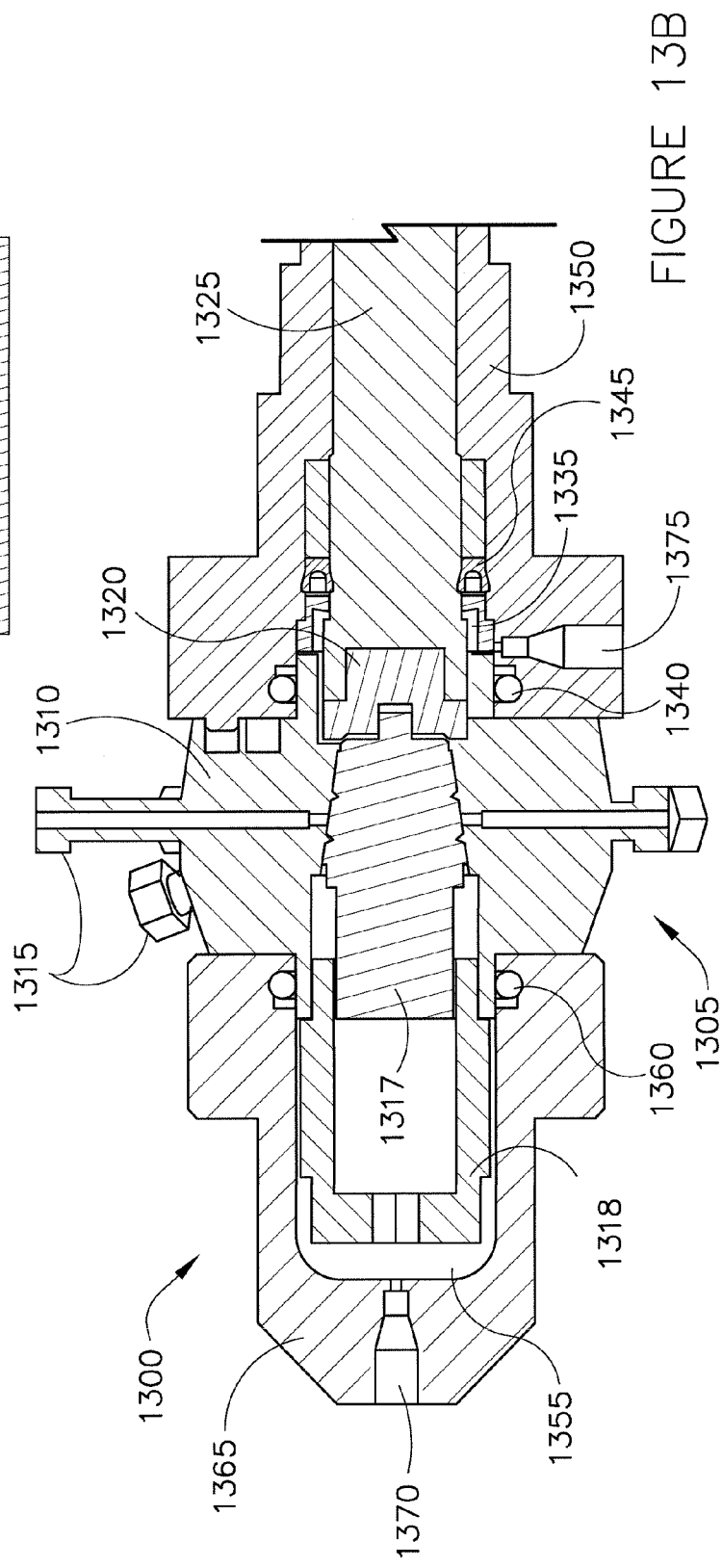

HIGH PRESSURE PARALLEL FIXED BED REACTOR AND METHOD

This application claims priority from U.S. Provisional patent application No. 60/854,760, filed Oct. 26, 2006, which is incorporated herein by reference in its entirety.

BACKGROUND OF INVENTION

The present invention relates generally to systems for high speed analysis of combinatorial libraries by contacting a plurality of library members simultaneously with a test fluid under high pressures, and more particularly, to an apparatus and method for screening library members based on each member's ability to catalyze the conversion of fluid reactants.

Combinatorial chemistry refers to methods for creating chemical libraries—vast collections of compounds of varying properties—that are tested or screened in order to identify a subset of promising compounds. Depending on how they are made, libraries may consist of substances free in solution, bound to solid supports, or arrayed on a solid surface.

The advent of combinatorial chemistry promises to change the discovery and development of new and useful materials. For example, workers in the pharmaceutical industry have successfully used such techniques to dramatically increase the speed of drug discovery. Material scientists have employed combinatorial methods to develop novel high temperature superconductors, magnetoresistive materials, and phosphors. More recently, scientists have applied combinatorial methods to catalyst development. See, for example, U.S. Pat. No. 5,985,356 "The Combinatorial Synthesis of Novel Materials" and U.S. Pat. No. 6,030,917 "Combinatorial Synthesis and Analysis of Organometallic Compounds and Catalysts", which are both herein incorporated by reference in their entirety.

Once a researcher creates a combinatorial library, he or she must screen tens, hundreds or even thousands of compounds. Existing analytical methods and devices, which were originally designed to characterize a relatively small number of compounds, are often ill-suited to screen combinatorial libraries. This is true in catalyst research where, up until now, there has been little need to rapidly test or characterize large numbers of compounds at one time.

In traditional catalyst development, for example, researchers synthesize relatively large amounts of a candidate compound. They then test the compound to determine whether it warrants further study. For solid phase catalysts, this initial testing involves confining the compound in a pressure vessel, and then contacting the compound with one or more fluid phase reactants at a particular temperature, pressure and flow rate. If the compound produces some minimal level of reactant conversion to a desired product, the compound undergoes more thorough characterization in a later step.

Because synthesis consumes a large fraction of the development cycle in traditional catalyst studies, researchers have expended little effort to speed up the screening step. Thus, although test reactors have been steadily improved over the years, most were simply automated to reduce labor needed to operate them. Even automated catalyst screening devices comprised of multiple reaction vessels were operated sequentially, so that the reaction time for a group of candidate compounds was about the same as could be achieved with a single-vessel reactor.

Conventional catalyst screening devices have other problems as well. For example, traditional experimental fixed bed reactors require relatively large catalyst samples. This makes them impracticable for screening combinatorial libraries. With combinatorial methods, one obtains increased chemical diversity at the expense of sample size. Individual library members may therefore consist of no more than a milligram (mg) or so of material. In contrast, conventional fixed bed reactors typically require 10 g or more of each candidate compound.

Recently, parallel fixed bed reactors have been developed to address many of these problems. See, for example, U.S. Pat. No. 6,149,882 "Parallel Fixed Bed Reactor And Fluid Contacting Apparatus and Method", and co-pending U.S. patent application Ser. No. 11/145,050 (Publication No. 2006-0006065) "Microfluidic Fluid Distribution Manifold For Use With Multi-Channel Reactor Systems" both of which are herein incorporated by reference in their entirety. However the pressure and temperature operating parameters of these reactor systems are limited by the various components such as seals, valves, etc.

High pressure sealing at elevated temperatures (typically above about 1000 psig and 100° C.) of fluid valves (especially gas) is difficult due to the high pressure differential of the sealed fluid to atmosphere. High contact loads are typically required at seal surfaces which limit the ability of the valve to have the moving parts required for directing the gases to various ports.

The present invention overcomes, or at least minimizes, one or more of the problems set forth above.

SUMMARY OF INVENTION

In accordance with a first aspect of the present invention, the invention is directed to a method of screening members of a combinatorial library. The method includes confining a group of library members in a plurality of vessels, enclosing the plurality of vessels in a chamber, supplying a gas substantially into the chamber to pressurize the chamber above atmospheric pressure, contacting each of the confined library members with a test fluid by flowing the test fluid through each of the vessels under reaction conditions comprising a pressure in each of the vessels during the contacting step substantially above atmospheric pressure, detecting changes in the test fluid following contact with each of the confined library members, and relating changes in the test fluid to a property of each of the library members.

In accordance with a second aspect of the present invention, the invention is directed to a system for evaluating four or more catalysts. The system includes four or more reactors, each of the four or more reactors having a reaction cavity, an inlet port in fluid communication with the reaction cavity for receiving a reactant feed stream into the reaction cavity, an outlet port in fluid communication with the reaction cavity for discharging a reactor effluent stream out of the reaction cavity, an inlet fluid distribution system for providing fluid communication between at least one fluid source and each of the four or more reactors, an analytical measurement system for evaluating reaction products or unreacted reactants in the reaction cavity or in the reactor effluent stream of each of the four or more reactors, an outlet fluid distribution system for providing fluid communication between the analytical measurement system and each of the four or more reactors, a housing for enclosing the reactors, the housing defining a pressure chamber, wherein the housing is configured to sustain a pressure substantially above atmospheric pressure, and an inlet port in fluid communication with the housing for pressurizing the pressure chamber from an external pressure sources.

Other features, objects and advantages of the present invention will be in part apparent to those skilled in art and in part pointed out hereinafter. All references cited in the instant specification are incorporated by reference for all purposes. Moreover, as the patent and non-patent literature relating to the subject matter disclosed and/or claimed herein is substantial, many relevant references are available to a skilled artisan that will provide further instruction with respect to such subject matter.

BRIEF DESCRIPTION OF THE DRAWINGS

FIG. 4A is a side cross-sectional view of an embodiment of the present invention. FIG. 4B is a perspective view of the embodiment shown in FIG. 4A.

FIG. 8A is an exploded view of an exemplary flow chip assembly for use in one embodiment of the present invention.

FIG. 8B is bottom perspective view of an assembled version of the chip assembly of FIG. 8A.

FIG. 8C is an exploded perspective view of an exemplary reactor module including the flow chip assembly of FIG. 8A.

FIGS. 9A and 9B are cross-sectional side views of the portion of an exemplary reactor assembly including a selection valve.

FIGS. 13A and 13B are schematic drawings of one embodiment of a multi-port selection valve suitable for use in high-pressure, high-temperature applications.

DETAILED DESCRIPTION OF THE INVENTION

Figure 1:
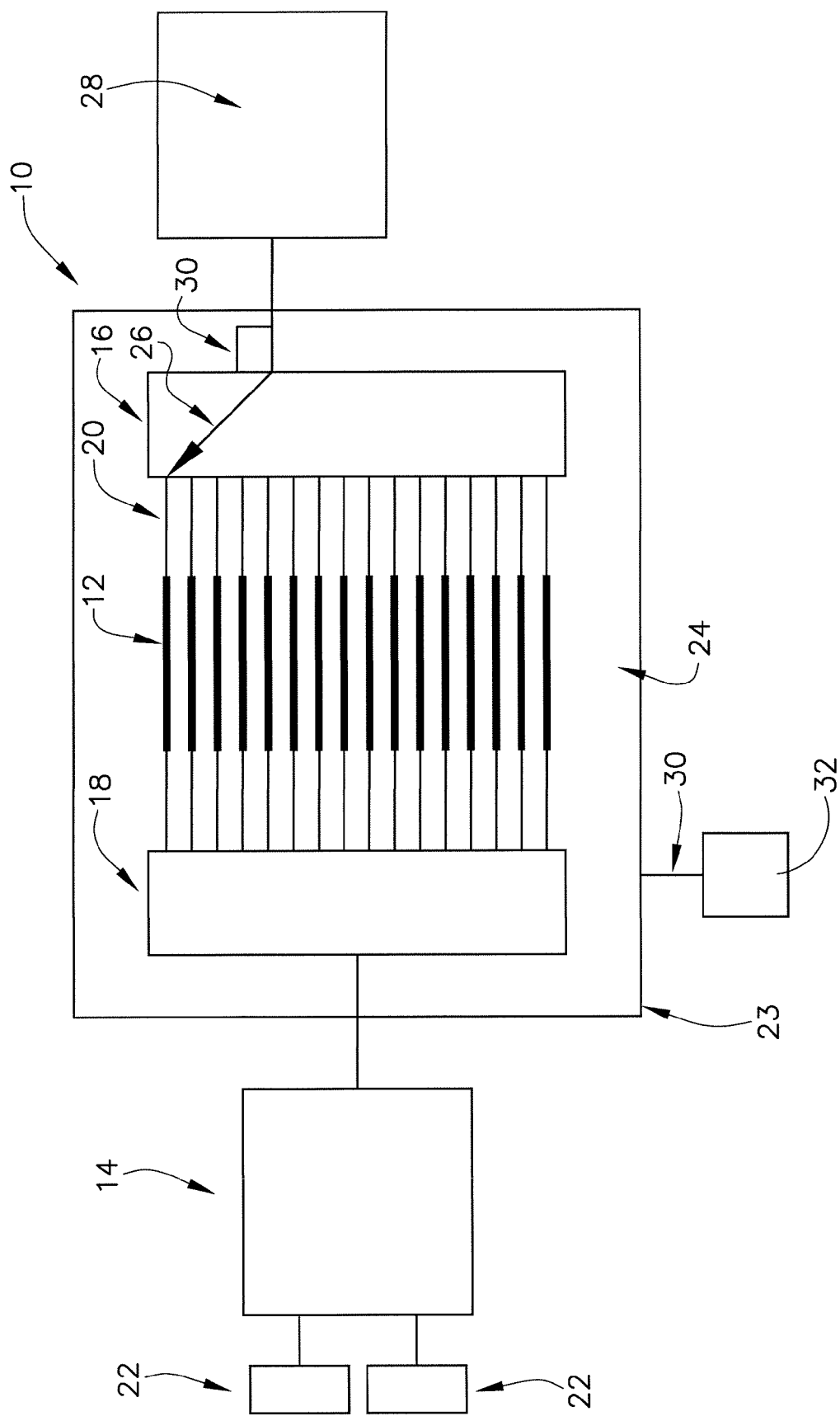
FIG. 1 is a schematic drawing of one embodiment of an apparatus for rapidly screening members of a combinatorial library.

The present invention provides an apparatus and method for rapidly screening members of a combinatorial library, preferably at high pressures. High throughput screening is achieved by contacting a group of library members with about equal amounts of a test fluid. Screening can be simultaneous for two or more library members or carried out in a rapid serial manner Changes in the test fluid resulting from contact with library members are used to identify members worthy of further study. In the following disclosure, the term "fluid" refers to any substance that will deform continuously under the action of a shear force, including both gases and liquids.

The apparatus and method can be used to screen library members based on any property that can be discerned by detecting or measuring changes in a test fluid following contact with a library member. Thus, for example, library members can be screened for catalytic activity by contacting each library member with a reactive fluid. The best performing library members are those that result in the highest concentration of a desired reaction product in the test fluid following contact.

The disclosed invention is not limited to screening catalysts, but can be used for rapid screening of many different types of materials. For example, the method and apparatus can be used to screen library members based on their ability to filter out or adsorb a specific gas species. The concentration of that gas species in a fluid stream following contact with a particular library member is inversely proportional to the particular material's performance. Similarly, polymeric materials synthesized using combinatorial methods can be screened for thermal stability by measuring the concentration of gaseous decomposition products in an inert fluid stream in contact with heated library members. The amount of decomposition product evolved by a particular polymeric material is a measure of that material's thermal stability.

Reactor systems disclosed in U.S. Pat. No. 6,149,882 "Parallel Fixed Bed Reactor And Fluid Contacting Apparatus and Method", U.S. Pat. No. 6,749,814 "Chemical Processing Microsystems, Diffusion-Mixed Microreactors And Methods For Preparing And Using Same", co-pending U.S. patent application Ser. No. 11/145,050 (Publication No. 2006-0006065) "Microfluidic Fluid Distribution Manifold For Use With Multi-Channel Reactor Systems" co-pending U.S. patent application Ser. No. 09/801,390 (Publication No. 2002-0048536) "Parallel Flow Process Optimization Reactor" and co-pending U.S. patent application Ser. No. 10/900,612 (Publication No. 2005-0056787) "Parallel Infrared Spectroscopy Apparatus and Method" all of which are herein incorporated by reference in their entirety, describe various reactor systems. These systems utilize many parts, such as sealing, coupling, fitting, and valve elements. Conventional components cannot withstand high pressure differentials that result when those systems run desirable high pressure reactions. Elements that can operate under high pressure differentials can be costly and difficult to maintain and in some instance are not commercially available. At higher pressures in the reaction vessels, the pressure differential between the surrounding atmosphere and the reactor is high, and results in the elements leaking or breaking, thus compromising the experiment or reaction. The present invention generally addresses this problem by providing a housing that encloses the reactor vessels and other elements of the system (such as the feed splitting, and outlet or analytical stream selection components), defining a pressure chamber that can be pressurized to high pressure levels. The pressure chamber is not in fluid communication with the reaction cavities or the fluid streams of the reactors, but pressurizes the surrounding atmosphere. When the reactor is run at high pressure, this provides a low pressure differential between the reactor components and the surrounding atmosphere (the pressurized chamber). This reduces the need for and number of high pressure components required. By adding a pressure chamber around the valve mating parts that is controlled within a small differential pressure of the sealed gas pressure, existing low pressure sealing technology can be used. The housing can operate at very high operating pressures while a single high pressure seal is maintained at a lower temperature. Also, flow distribution controllers, such as a flow splitting chip can be located upstream of the reaction vessels and provides flow rate uniformity to a plurality of channels independent of reaction pressures allowing uniform feed rates at near atmospheric pressure.

The invention is described in further detail below with reference to the figures, in which like items are numbered the same in the several figures.

FIG. 1 schematically shows one embodiment of an apparatus for rapidly screening members of a combinatorial library. The screening apparatus 10 is comprised of a plurality of vessels 12 for receiving members of the combinatorial library. Each of the vessels 12 is in fluid communication with a flow splitting device 18 (such as a microfluidic fluid distribution manifold), which is in fluid communication with one or more reactant reservoirs 22 respectively, optionally via a manifold 14 in embodiments where multiple fluid sources are combined. The vessels 12 are also in fluid communication with an exit control volume 16 through outlet conduits 20, respectively. The number of reactor vessels 12 is not critical, and is specifically at least four vessels, more specifically at least eight vessels, more specifically at least twelve vessels, more specifically at least sixteen vessels, more specifically at least twenty four vessels, more specifically at least thirty six vessels, more specifically at least forty eight vessels, and even more specifically at least sixty four vessels. The exit control volume 16 is generally any pressure-controlled region external to the vessel assembly 12.

Members of a combinatorial library are screened by simultaneously contacting a subset of library members with nearly equal amounts of test fluid. The test fluid is prepared by combining fluid streams from fluid sources 22 in a combining manifold 14, which is in fluid communication with the flow splitting device 18 and the vessels 12. During screening, the test fluid flows through the flow splitting device 18 and through each of the vessels 12. In one embodiment, the test fluid is a gas, in another embodiment, the test fluid is a liquid, and in another embodiment, the test fluid comprises a gas and a liquid.

Typically, solid library members are supplied to each of the vessels 12 in the form of a fixed bed: the library members are either supported on solid particles or are themselves granular or porous solids. In such cases, the test fluid flows through the interstices in the fixed bed, ensuring intimate contact between the test fluid and the library member Similarly, liquid library members are confined within the vessels 12 by capillary forces, and fluid contact occurs by bubbling test gas through the vessels 12. Following fluid/solid or fluid/liquid contacting, the test fluid exits each of the vessels 12 through outlet conduits 20 that convey the test fluid to the exit control volume 16. In another embodiment, the solid members can be applied to a support member, such as an alumina rod or spheres, and inserted into the vessels.

Most vessel effluent dumps directly into the exit control volume 16. However, test fluid from selected vessels 12 can be routed from the outlet conduits 20 through a sample bypass 26 (such as via a selection valve or a sample probe) to a detector 28, which measures changes in the test fluid resulting from contact with a library member. In one embodiment, almost all of the fluid in the sample bypass 26 is returned to the exit control volume 16 through a return line 30; only a small fraction is actually sent to the detector 28 for analysis. In another embodiment, all of the fluid sample is sent to the detector for analysis. The ability of the detector 28 to analyze test fluid from more than one of the vessels 12 simultaneously will depend on the type of detector 28. A useful detector 28 for screening catalysts includes a gas chromatograph (GC), which can measure concentration of a desired reaction product in vessel effluent. Other useful detectors include mass spectrometers, as well as ultraviolet, visible, and infrared spectrometers.

A housing 23 encloses the vessels 12 and preferably the flow splitting device 18 and sample bypass 26, providing a chamber 24 that can be pressurized to high pressures, allowing reactions in the vessels to occur at high pressures while applying a low pressure differential on the reactor components in the chamber, such as coupling, fittings and valves. The housing 23 includes an inlet port 30 for pressurizing the pressure chamber 24 from an external pressure source 32.

Figure 2:
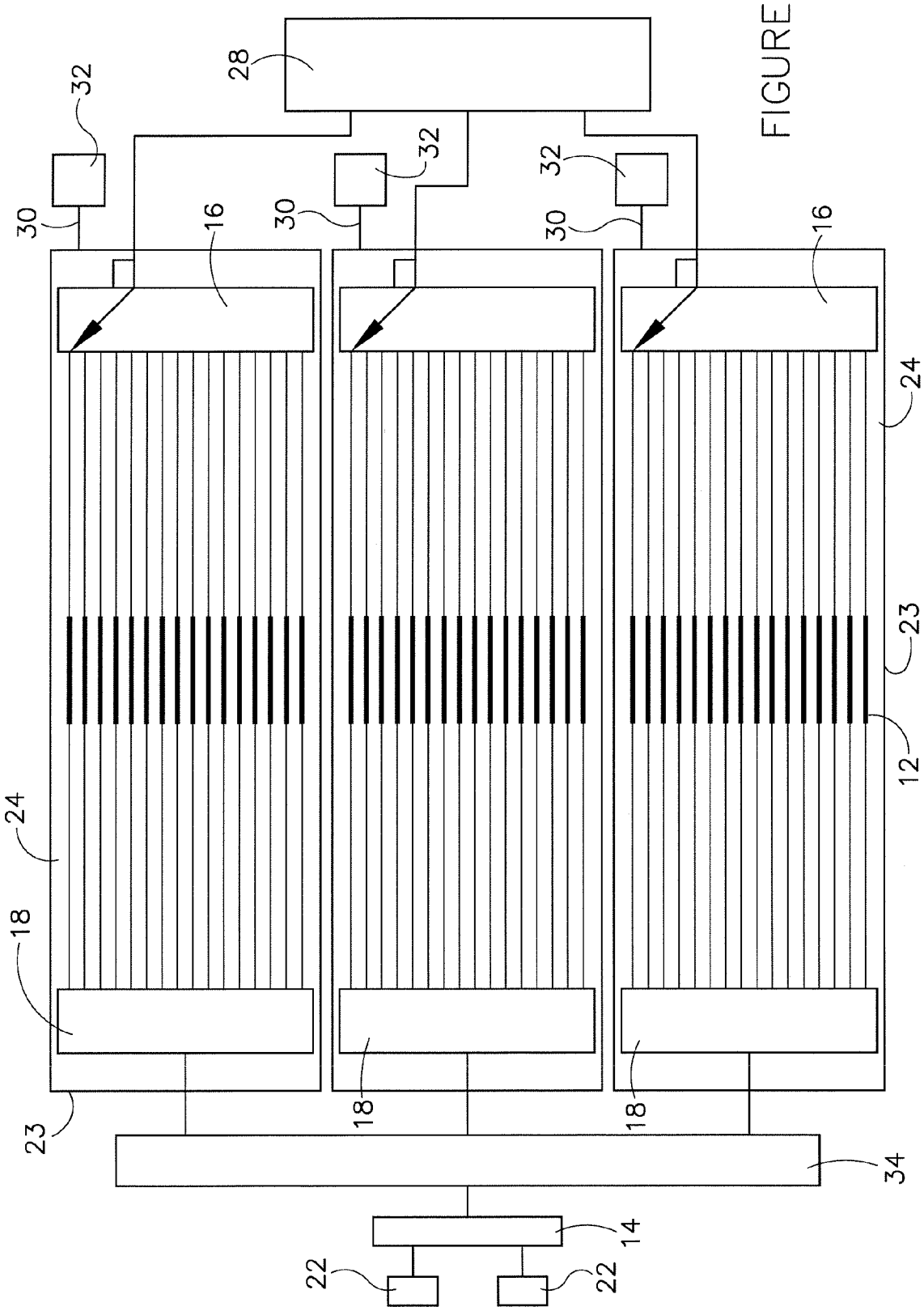
FIG. 2 is a schematic drawing of one embodiment of an apparatus for rapidly screening members of a combinatorial library.

The embodiment shown in FIG. 1 can be considered a single reactor module that can be combined with other reactor modules to provide even greater throughput capabilities. For example, FIG. 2 schematically shows one embodiment of an apparatus for rapidly screening members of a combinatorial library that includes three reactor modules. In embodiments with multiple modules, an additional manifold 34 is in fluid communication with the combining manifold 14 and the flow splitting device 18 for each module. In the embodiment of FIG. 2, the manifold 34 splits the combined incoming fluid stream into three equal streams to be delivered to each reactor module. Although the screening apparatus depicted in FIG. 2 has a detector 28 that can analyze vessel effluent from three vessels 12 simultaneously, the number of detectors 28 can be varied.

Fluid Handling System

Figure 3:
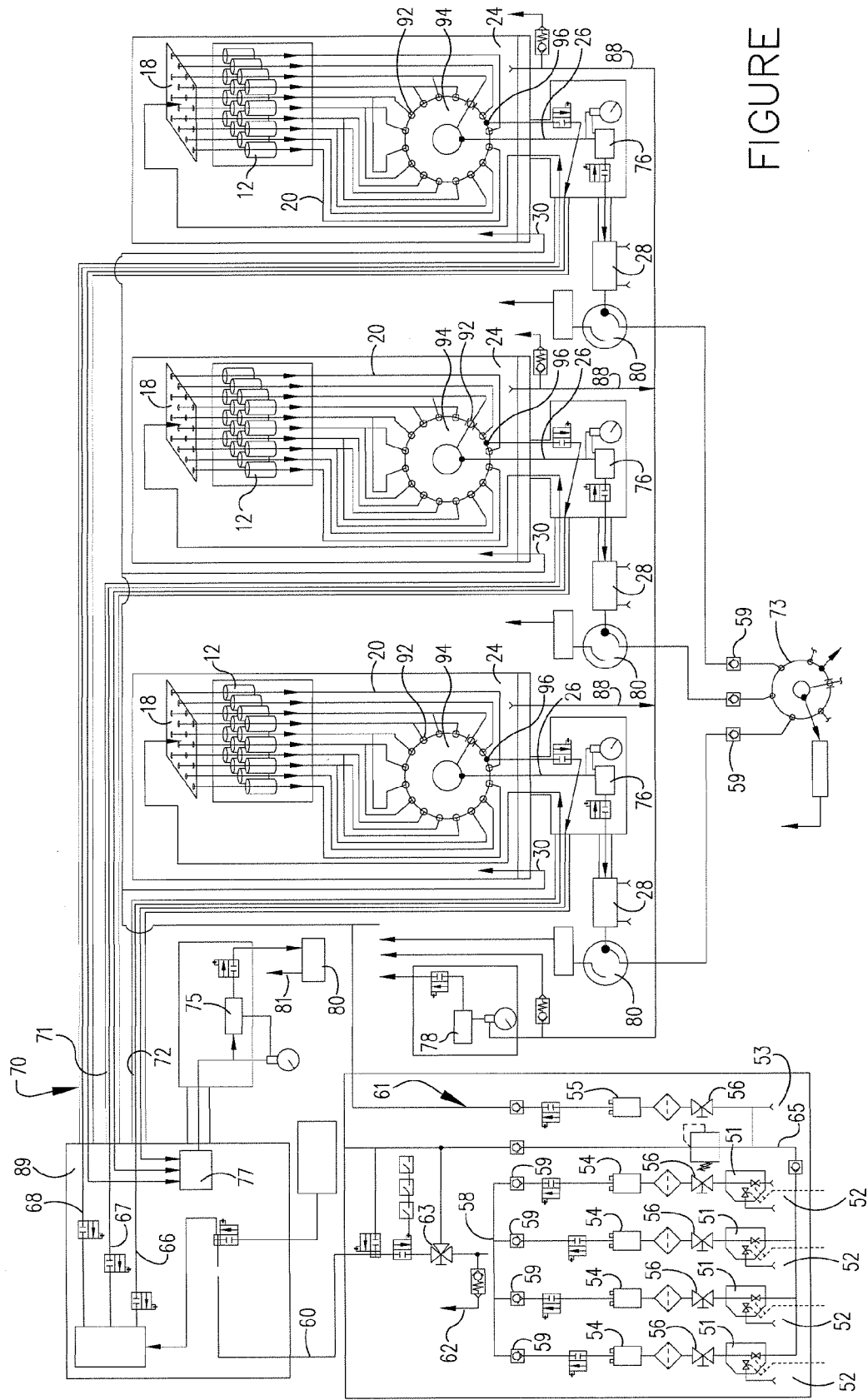
FIG. 3 is a schematic drawing of a fluid handling system of the screening apparatus.

The reactor system of the present invention includes a fluid handling system. Further details of one embodiment of the fluid handling system are shown in FIG. 3. For clarity, FIG. 3 illustrates an exemplary fluid handling system suitable for screening potential catalysts utilizing a system with three modules, each module having sixteen reactor vessels, similar to the schematic of FIG. 2.

Test fluid sources 52 are in fluid connection with conventional mass flow controllers 54 such as the Celerity Model C7361. The mass flow controllers 54 adjust the amount of each test fluid constituent. Isolation valves 56 allow each fluid source to be taken off line, using manual valves upstream of each controller or pneumatic on/off valves upstream of each mass flow controller. Fluids from individual sources 52 flow through the mass flow controllers 54 and are combined in a manifold 58. From there, the test fluid flows through a feed line 60. If necessary, the test fluid can vent through an exhaust port 62.

An inert fluid source 53, such as nitrogen gas, is in fluid connection with a mass flow controller 55. The inert gas flows through the mass flow controller 55. From there, the inert gas flows through a feed line 61, where it is fed through the inlet 30 of the housing 25 and into the chamber 24 of each module. The pressure in the chamber 24 is controlled by a back pressure controller. The inert fluid source 53 can also be fed to the test fluid mass flow controllers 56 through feed line 65. Valves 51 can be used to turn on or shut off inert or test fluid flow to the mass flow controllers 54. The inert fluid can also be routed to feed line 60 via a three way valve 63 located upstream of the manifold 58 for switching between process gas and the inert gas. Check valves 59 may also be utilized throughout the flow paths in order to prevent back flow of fluids in the system.

The line is fed into an upstream heated flow assembly 89 which can be heated up to about 200° C. A feed line transducer 66 monitors pressure immediately upstream of a three port manifold 64 that splits the feed stream 60 into three equal streams 66 67 68. The streams enter heated transfer lines 70 71 72 where they are directed into the housing and to the fluid splitting device 18. Upon entering the fluid splitting device 18 (e.g., a microfluidic manifold distribution chip), the streams are diverted into an appropriate amount of streams to be fed into inlets of the reactors, in the case of FIG. 3, the streams 70 71 72 are each split into sixteen streams to be fed into sixteen reactors in each module.

The properties of some library members may change during exposure to test fluid. For example, a sample may exhibit high catalytic activity during initial contact with a reactive fluid, but a short time later, may show a precipitous decline in activity. Conversely, a sample may show an increase in catalytic activity with elapsed contact time. In such cases, one must ensure that the time from initial contact with the test fluid to detection of changes in the test fluid is about the same for each sample; otherwise, when using a combination of parallel and serial screening, a sample's perceived performance will depend on position within the screening cycle.

The test fluid exits the vessels 12 through outlet conduits 20, and eventually vents into the exit control volume 16. Each of the outlet conduits 20 is in fluid connection with one of a plurality of inlet ports 92 of a selection valve 94, such as a 16-port selection valve. The selection valve selectively diverts most of the vessel effluent streams directly into the exit control volume 16 via a common exhaust port 96. However, the selection valve 94 selectively routes fluid from one of the vessels 12 through a sample bypass 26 to a detector 28 via a heated line, which measures changes in the test fluid resulting from contact with a library member. Fluid in the sample bypass 26 can be returned to the exit control volume 16 through a return line 28 or can be sent to an outlet valve 73, such as a 6-port Valco valve where the flow can be measured and vented. Although the selection valves 94 depicted in FIG. 3 each receive fluid from sixteen vessels 12, the selection valve 94 can be designed to accommodate more or less vessels 12. Moreover, the fluid handling system 50 can comprise more than one selection valve 94, so that fluid from two or more vessels 12 can be analyzed simultaneously using either multiple detectors or a multiple channel detector. In other embodiments, (not shown) a sample probe can be used to divert a selected fluid to a detector, such as a mass spectrometer or a gas chromatograph, while the other streams are combined and diverted to the exit control volume.

The fluid handling system shown in FIG. 3 can use a sampling valve (not shown) to send a fixed volume of fluid to the detector without upsetting the volumetric flow rate throughout the rest of the fluid handling system.

Referring once again to FIG. 1, an aspect of the screening apparatus 10 is that it apportions the test fluid about equally between each of the vessels 12. This is important because the extent of change in the test fluid following contact with a library member depends on, among other things, the time a given amount of test fluid contacts the library member.

The test fluid is split about equally among the vessels 12 in at least two ways. First, the flow splitting device 18 includes passive restriction that is the greatest resistance to flow in the system. In a preferred embodiment, the passive restriction is in the form of micromachined channels of a microfluidic fluid distribution chip having equally designed channels for each fluid stream. Because fluid flow resistance is greatest in the splitting device 18 and varies little among individual channels 18, the test fluid is apportioned about equally between each of the vessels 12. Furthermore, because the restriction is upstream of the vessels 12 in the embodiment shown in FIG. 1, flow rate through the vessels 12 is mainly a function of the applied pressure upstream of the restriction, and the pressure in each of the vessels 12 is about equal to the pressure in the exit control volume 16 or downstream. Thus, the pressure in the vessels 12 can be controlled by adjusting the pressure in the exit control volume 16, generally independently of flow rate through the vessels 12. The pressure is controlled downstream of the reactor vessels 12 by the use of back pressure controllers. For fluid that has been sent to the exit control volume 16, the fluid streams are sent via the heated transfer lines 70 71 72 to a downstream three port manifold 77 where the streams are combined, sent through a back pressure controller 75, and a vent 81. The streams selected for analysis are sent through a back pressure controller 76, to the detector 28 and vented 82. Each slow path also includes a knockout pot 80 to trap or remove any liquids from the stream prior to venting.

The pressure chambers 24 are also pressure controlled via back pressure controllers to match the pressure in the reaction vessels 12. By matching the pressure in the chamber to the pressure in the reaction vessels 12, the reactor vessel components only need to seal against the pressure differential. The chambers 24 include outlet lines 88 that are in fluid communication with a back pressure controller 78 to maintain a desired pressure in the chamber 24. Preferably, the pressure chamber and the reactor vessels are pressurized and de-pressurized simultaneously to prevent a large pressure differential on reactor components. In one embodiment, the pressure in the chamber 24 is automatically adjusted to track the reactor vessel pressure. The desired pressure differential is set, and when the pressure in the reactor vessel 12 changes, the pressure in the chamber automatically adjusts to maintain the desired pressure differential.

FIGS. 4A and 4B show a side cross-sectional view and a perspective view, respectively of an embodiment of the present invention. The reactor system comprises a main fluid inlet line 400 that is split into equal reactor inlet lines 404 for distribution to the reactor vessels 12, via a microfluidic flow distribution chip 402. Each reactor inlet line 404 is in communication with the inlet of a reactor vessel 12. The outlet of each reactor vessel 12 is in communication with outlet lines 406. The outlet lines feed to a selection valve 408, which sends one stream to a detector and combines the remaining streams to be sent to the exit control volume. The main inlet line 400, and the two lines leaving the selection valve 408 enter and exit the housing 25 via a heated transfer line 410 which is in fluid communication with an outlet channel 406.

As shown in FIGS. 4A and 4B, the housing 25 that encloses the reactor vessels, distribution chip 402 and selection valve 408 comprises two sections; a base member 412 and a top member (or cover) 414. The combination of the base 412 and cover 414 form a chamber 24 to enclose the reactor vessels 12 as well as the microfluidic fluid distribution manifold 402 and the selection valve 408. Internal surfaces of the base 412 and cover 414 define an internal cavity which fauns the pressure chamber 24. The pressure chamber 24 may have any volume necessary to encompass the system components to be pressurized. The base member 412 can have any necessary shape, such as a plate. The cover 414 can also have any suitable shape to provide suitable interaction with the base and provide an enclosure for the reactor components. In one embodiment, the cover 414 is bell-shaped. The base 412 and the cover 414 can be connected by many suitable techniques. In one embodiment, the base 412 has a first surface 416 that is configured to contact a second surface 418 of the cover 414. When brought into contact, the base 412 and the cover 414 form a housing that encloses the various reactor components and defines a pressure chamber 24. In one embodiment, the cover 414 includes a groove 420 extending around a periphery thereof for receiving a sealing gasket 422. The gasket 422 is interposed between the base 412 and cover 414 to provide a seal therebetween. The groove 420 for the gasket 422 may be machined into either a first surface of the base 412, or a second surface of cover 414. The gasket 422 may be an o-ring formed from PTFE, neoprene, butyl rubber, Teflon coated elastomer, Viton, expanded Teflon, graphite, or Kalrez, for example.

Any suitable type of fastener may be used to hold the base and cover together. In one embodiment, a split clamp 424 is configured to engage the base 412 and cover 414 and keep the base and cover together under high pressure. The split clamp 424 is self-locking under pressure, and can provide additional sealing and is easily engaged and disengaged in order to close the housing or access the reactor components. In another embodiment, the cover 414 includes a periphery flange (not shown) configured to mate with a periphery flange (not shown) extending from the base member 412. The flanges of the cover 412 and base 414 can include a plurality of openings for receiving bolts, screws, or other fasteners.

The housing includes an inlet port in fluid communication with the pressure chamber 24. In one embodiment, the inlet is a high pressure coupling for attachment of a fluid line. In another embodiment a quick release fitting can be coupled to the inlet port for attaching the port to a flexible hose or rigid tube (not shown) connected to a pressure supply device. The flexible hose or rigid gas supply tube may also be left connected and the fill valve open during an experiment.

In one embodiment, a fill valve can be optionally attached to the inlet port to control the application of pressure to the vessel. The fill valve may have a manual or electronic pressure control valve. A pressure sensor (not shown) may be inserted inline with the fill valve or inserted into the pressure chamber 24 to monitor the pressure within the chamber 24. In another embodiment, the housing 25 includes an outlet including a high pressure coupling for attachment of a fluid line. The fluid line is in fluid communication with a back pressure controller which controls the pressure in the chamber 24.

The inlet supply system may allow for a series of purging, venting, or pressurization cycles, with one or more gases or with vacuum without disconnecting the supply lines. The pressure source may be an inert gas such as nitrogen, argon, helium, carbon dioxide, or air. The gases can also be heated or cooled to adjust the temperature in the chamber.

The base 412 and cover 414 may be formed from aluminum, titanium, steel, or any other suitable material. The material of the housing is preferably selected to be chemically inert to the pressurization gas, and allow the system to operate at high temperature, specifically, greater than 100° C., more specifically greater than 150° C., more specifically greater than 200° C., more specifically greater than 250° C., more specifically greater than 300° C., more specifically greater than 350° C., more specifically greater than 400° C., more specifically greater than 450° C., more specifically greater than 500° C. more specifically greater than 550° C., more specifically greater than 600° C., and even more specifically greater than 650° C. The material of the housing is also preferably selected to maintain high pressure, specifically, greater than 200 psi, more specifically, greater than 500 psi, more specifically, greater than 750 psi, more specifically, greater than 1000 psi, more specifically, greater than 1200 psi, more specifically, greater than 1500 psi, more specifically, greater than 1750 psi, and even more specifically, greater than 2000 psi. For example, if the apparatus is to be operated at 250 psi and 150° C., 6061-T6 aluminum, which has been hard anodized, may be used. If the operating pressure is 1000 psi and operating temperature is 200° C., the material may be 17-4PH, H1100 stainless steel or 6Al-4V titanium. If the operating pressure is 2000 psi and operating temperature is 500° C., the material may be 316 stainless steel. In one embodiment, the cover 414 and base 412 are 316 stainless steel and the split clamp 424 is 17-4PH, H1150 stainless steel. For some applications, the stainless steel or other material may be coated or surface treated. It is to be understood that the temperature or pressure applied to the housing or the materials used to form the base 412 and cover 414 may be different than described herein without departing from the scope of the invention. The housing is preferably designed to withstand pressures substantially above atmospheric pressure (i.e., 14.7 psi).

Figure 5:
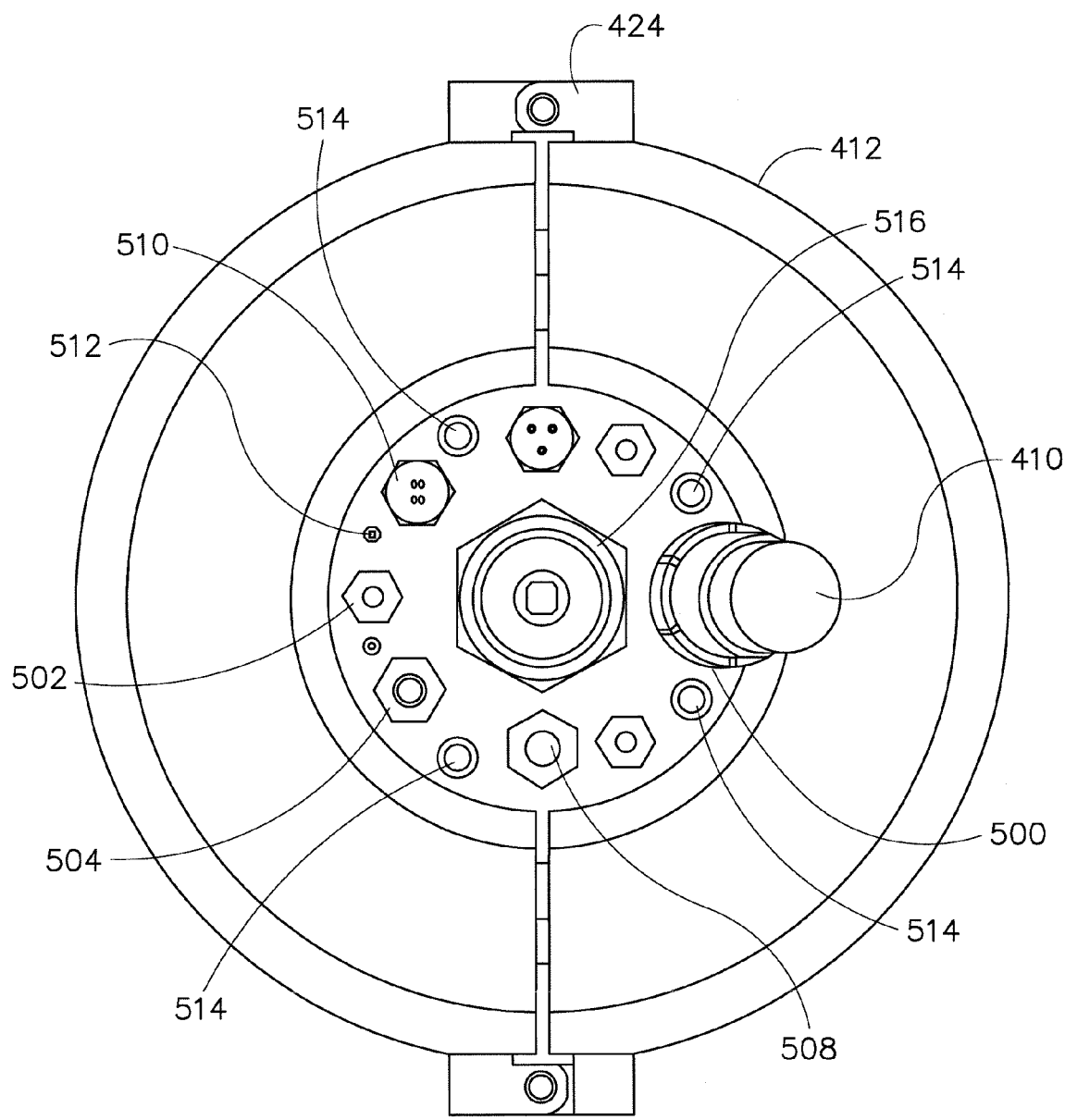
FIG. 5 is a bottom view of an embodiment of the bottom of the housing of the present invention.

FIG. 5 shows a bottom view of an embodiment of the bottom 412 of the housing 25 of the present invention. The bottom 412 acts as a feed through plate and provides the inlets and outlets for access to the reactor system inside the housing 25. The bottom 412 includes an opening 500 for the heated transfer line 410, which contains the main inlet stream that is directed to the inlet of the flow distribution chip, and the two outlet streams from the selection valve. The bottom 412 also includes the chamber gas inlet 502 and gas outlet 504 for pressurizing the chamber 24, high pressure feed through components for providing wires to a heating assembly for the flow chip 506 and the reactor heater 508, as well as optional feed throughs for thermocouples 510. The bottom 412 can also accommodate thermocouples 512 and heater cartridges 514. Finally, the bottom 412 has an access for the selection valve control shaft 516.

Figure 6A:
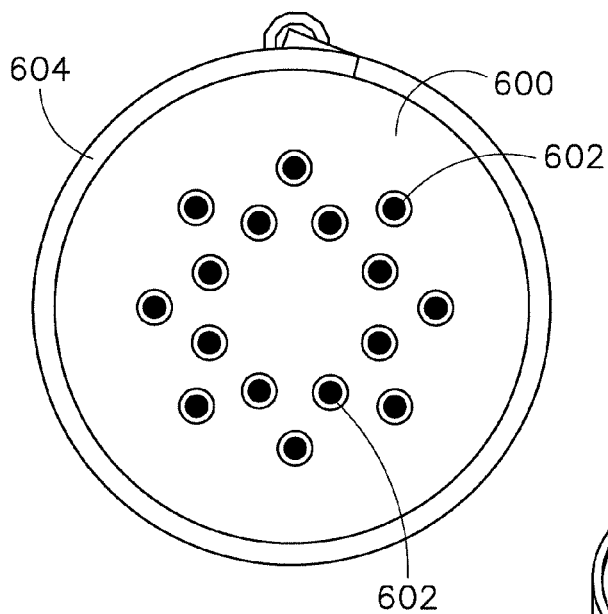
FIG. 6A is a top view of an exemplary reactor block that is used to hold and heat reactor vessels.
Figure 6B:
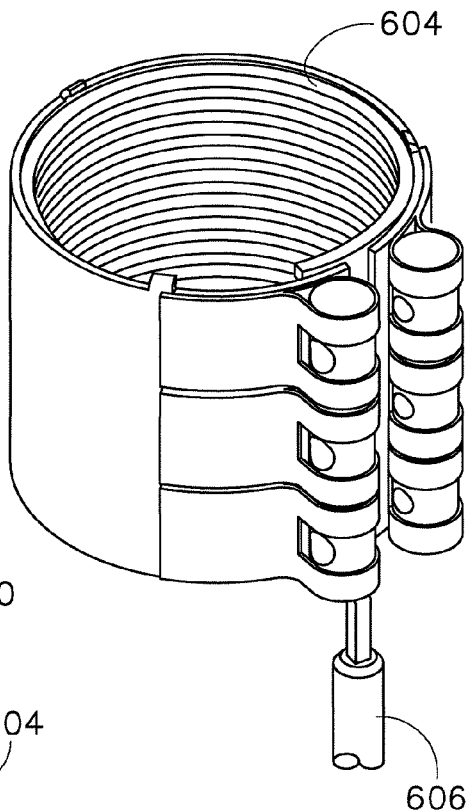
FIG. 6B is a perspective view of an exemplary heating device that can be used to heat the reactor block and the reactor vessels.
Figure 6C:
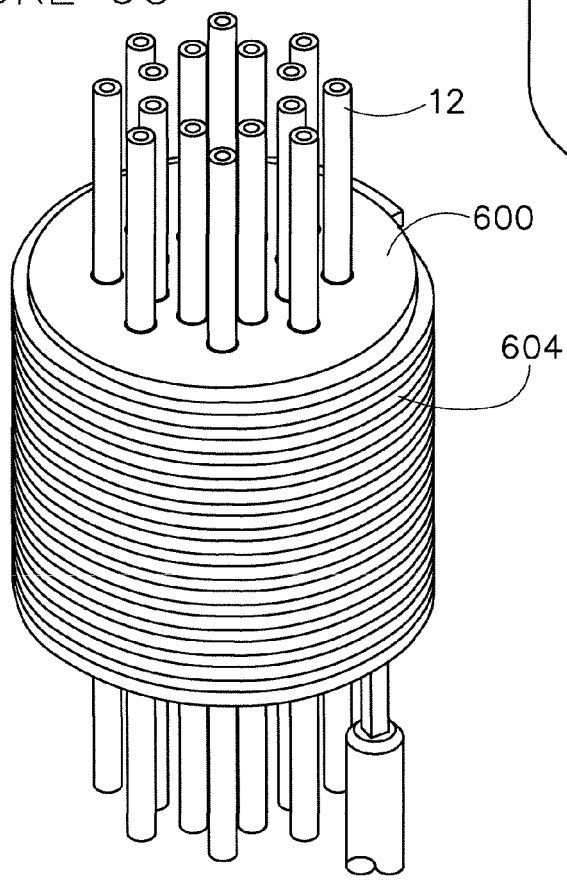
FIG. 6C is a perspective view of an exemplary reactor block, heater and the reactor vessels.

FIGS. 6A, 6B and 6C show various aspects of an embodiment of the reactor assembly of the present invention. FIG. 6A shows a top view of a reactor block 600 that is used to hold and heat the reactor vessels 12. The block 600 can be any material that is capable of conducting heat and operating at high temperatures. In one embodiment, the block is constructed of C360 brass. The reactor block 600 comprises throughbores 602 for holding the reactor vessels 12. In the embodiment shown in FIG. 6A, the throughbores 602 for holding sixteen reactor vessels are arranged in two concentric circles at eight equally spaced points. In one embodiment, the throughbores 602 are designed so that the radial gap between the reactor vessel and the throughbore wall is minimized (such as less than 0.002 in., more specifically less than 0.001 in.) in order to improve the heat transfer between the reactor vessels and the block. In another embodiment, the reactor vessels are integral with the block. FIG. 6B shows an embodiment of a heating device 604 that can be used to heat the reactor block 600 and the reactor vessels 12. In one embodiment, the heater is a coiled cable heater with an Iconel band clamp that allows temperature control up to 650° C. The heater is controlled through a wire 606 that is fed through the bottom 412 of the housing 25 and is externally controlled. FIG. 6C shows a perspective view of the reactor block 600, the coiled heater 604 and the reactor vessels 12.

Figure 7:
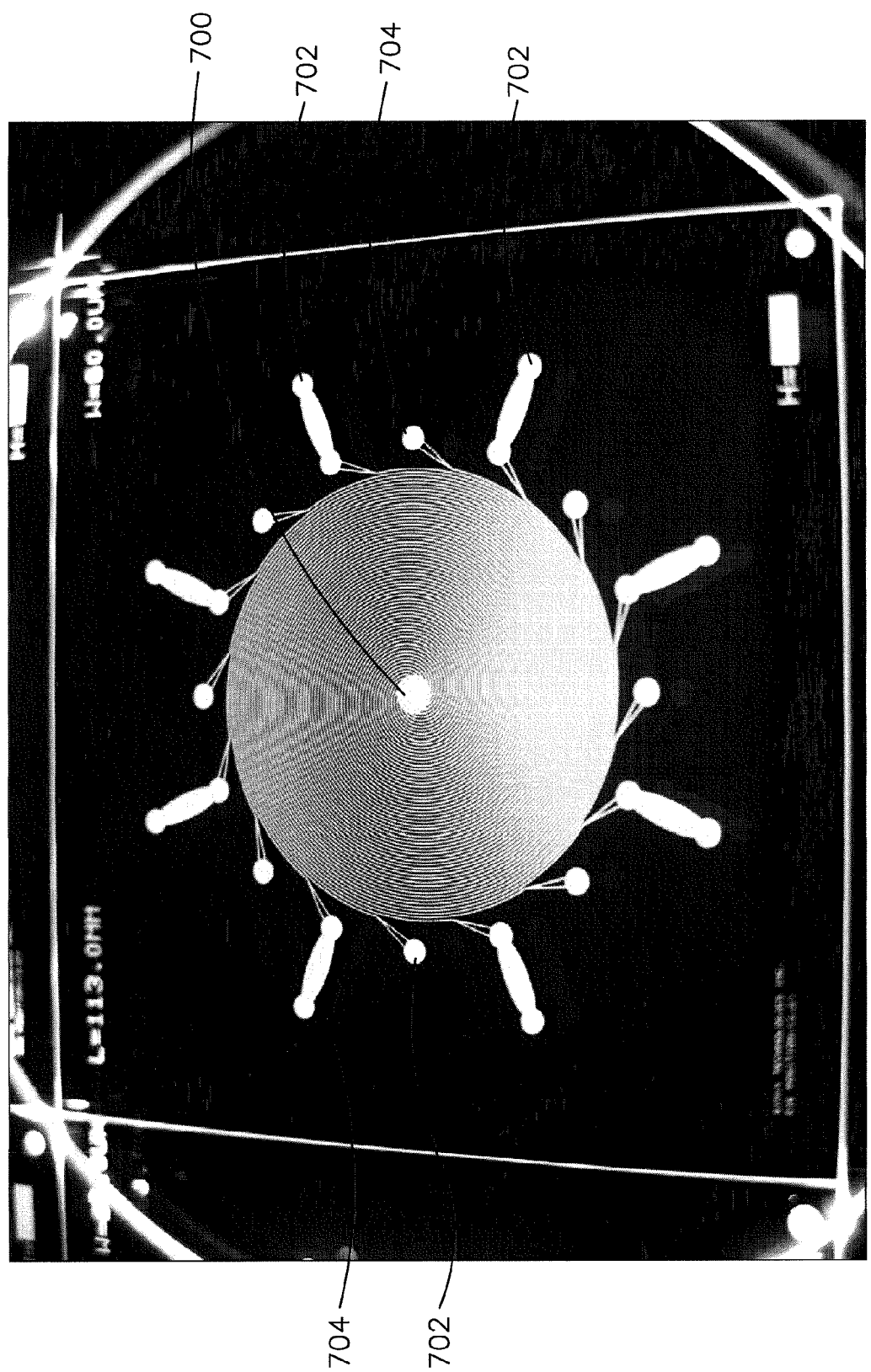
FIG. 7 shows an exemplary view of a microfluidic fluid distribution manifold.

FIG. 7 shows an embodiment of the flow splitting device 18, which is preferably a microfluidic fluid distribution manifold. Generally, the microfluidic fluid distribution manifold of the invention comprises a common port 700, and an independent port 702 and fluidic channel 704 for each reactor inlet, each of the channels 704 providing fluid communication between the common port 700 and a respective independent port 702. Thus in embodiments with four reactor inlets in a module, the microfluidic fluid distribution manifold has four independent ports and fluidic channels, in embodiments with eight reactor inlets in a module, the microfluidic fluid distribution manifold has eight independent ports and fluidic channels, in embodiments with twelve reactor inlets in a module, the microfluidic fluid distribution manifold has twelve independent ports and fluidic channels, and in embodiments with sixteen reactor inlets in a module, the microfluidic fluid distribution manifold has sixteen independent ports and fluidic channels. FIG. 7 shows an embodiment of a microfluidic fluid distribution manifold having a common port and sixteen independent ports and fluidic channels, designed to split an incoming fluidic stream into sixteen separate streams to feed sixteen reactor vessels. The single fluid stream is received at the common port, communicated through the fluidic channels, and discharged as separate split fluid streams through a respective one of the independent ports. The specifics of the designs of the microfluidic fluid distribution manifold that can be used in the reactor of the present invention are disclosed in U.S. Pat. No. 6,749,814 "Chemical Processing Microsystems, Diffusion-Mixed Microreactors And Methods For Preparing And Using Same" and co-pending U.S. patent application Ser. No. 11/145,050 (Publication No. 2006-0006065) "Microfluidic Fluid Distribution Manifold For Use With Multi-Channel Reactor Systems" both of which are hereby incorporated by reference in their entirety.

In one embodiment, at least a portion of each of the fluidic channels is spirally interleaved relative to the other fluidic channels. The spirally interleaved portion of each of the channels has a radius of curvature that increases with increasing distance from the common port. Specifically, the channels make more than 1.1 turns around the common port, and have substantially the same overall resistance to fluid flow. Specifically, each of the fluidic channels have an overall resistance to fluid flow measured between the common port and the respective independent ports, such that the overall resistance to fluid flow for each of the fluidic channels varies by not more than about 1%.

Also, the radius of curvature of each of the four or more fluidic channels can be substantially the same as other fluidic channels as a function of distance from the common port.

In one embodiment, the microfluidic flow distribution manifold is adapted for operation with fluids at a pressure of more than about 1400 psi, more specifically, more than about 1500 psi, and even more specifically, more than 1750 psi.

In another embodiment, the microfluidic flow distribution manifold includes one or more microfluidic filters adapted to filter non-fluidic contaminants from a fluid before the fluid is communicated through the fluidic channels. Specifically, the filters are disposed in the common port to filter non-fluidic contaminants from a fluid before the fluid is communicated through the spirally interleaved fluidic channels.

In another embodiment, the microfluidic flow distribution manifold is adapted for operation with gaseous fluids at a temperature of more than about 100° C., more specifically more than about 200° C.

In another embodiment, the fluidic channels 704, the common port 700 and the independent ports 702 are at least partially defined in a common channel layer. Specifically, the common channel layer has a first surface and an opposing second surface. The manifold also includes a base layer having a first and second surface, the second surface of the base layer being disposed adjacent the first surface of the channel layer, and a capping layer having a first and second surface, the first surface of the capping layer being disposed adjacent the second surface of the channel layer. The manifold also specifically includes a common aperture disposed through the base layer and in fluid communication with the common port. The manifold can also have independent apertures disposed through the base layer for each independent port. Each of the independent apertures is in fluid communication with one of the independent ports. Specifically, the common port, the independent ports and the microfluidic filter are microfabricated in a plurality of laminae comprising the common channel layer, a base layer having a first and second surface, the second surface of the base layer being disposed adjacent the first surface of the channel layer, and a capping layer having a first and second surface, the first surface of the capping layer being disposed adjacent the second surface of the channel layer.

FIG. 8A shows an exploded view of the flow chip assembly 800 for use in one embodiment of the present invention. The assembly includes a flow chip 802 as shown in FIG. 7, having a first surface and a second surface. The first surface includes the common port and the independent ports, and the second surface is the backside of the chip 802. The first surface of the flow chip 802 contacts a first surface of an interface manifold 804, which has a plurality of throughbores that correspond with each independent port and the common port, to provide a main inlet channel 824 into the flow chip and a plurality of outlet channels 826 from the flow chip that feed the inlets of the reactor vessels 12. The second surface of the flow chip contacts a compression plate 806, and the flow chip 802 and compression plate 806 are sandwiched between the interface manifold 804 and an assembly cover 808. The assembly cover 808 has an opening 809 for access of a compression element 822, such as a spring or Belleville washer assembly. An O-ring plate 810 that is configured to interface with the inlets of the reactor vessels 12 is attached to a second surface of the interface manifold 804. The O-ring plate 810 comprises a plurality of O-ring seals that correspond to the flow paths of the main incoming fluid stream and the split streams being delivered to the reactor vessels 12. The O-ring plate 810 is aligned with the interface manifold 804 and the interface manifold 804 is aligned with the assembly cover 808 with alignment pins 814 812. A bottom perspective view of an assembled version of the chip assembly 800 is shown in FIG. 8B.

FIG. 8C shows an exploded perspective view of the reactor module including the flow chip assembly 800. The flow chip assembly 800 interfaces with the reactor vessels 12 in the reactor block, such that the O-ring plate 810 interfaces with and seals the inlets of each of the reactor vessels 12. A support plate 816 aligns with the assembly cover 808 and is configured to interface with reactor module supports 818 to hold the flow chip assembly in place and allow compression force to be applied to the flow chip. A compression screw 820 is used to tighten the compression element in the flow chip assembly once the support plate 816 is interfaced with the reactor module supports 818. An assembled side cross-sectional view of the assembled flow chip assembly 800 interfaced with the reactor module is shown in FIG. 8D.

Figure 8E:
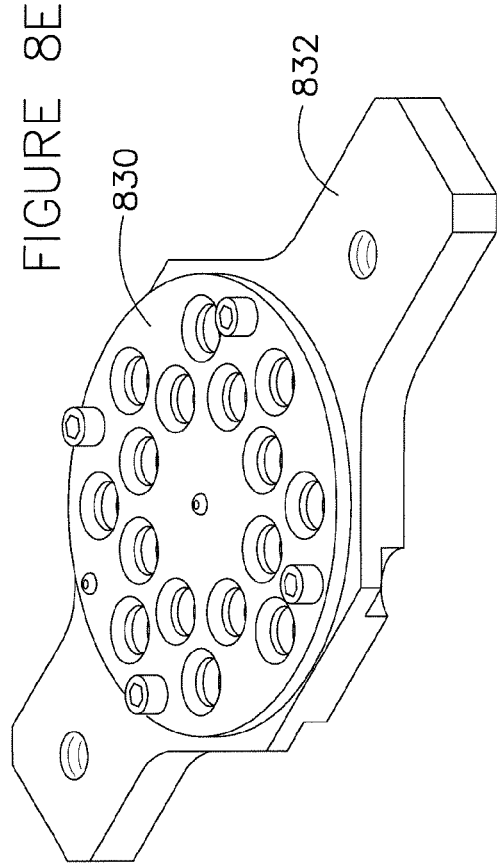
FIG. 8E is a perspective views of an exemplary bottom plate sealing assembly for the reactor vessels.
Figure 8F:
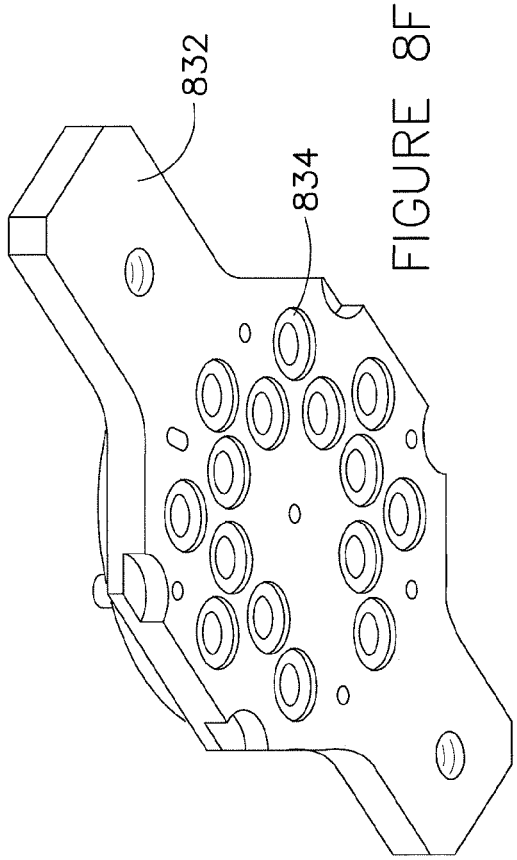
FIG. 8F is a bottom perspective view of the exemplary bottom plate sealing assembly of FIG. 8E.
Figure 8D:
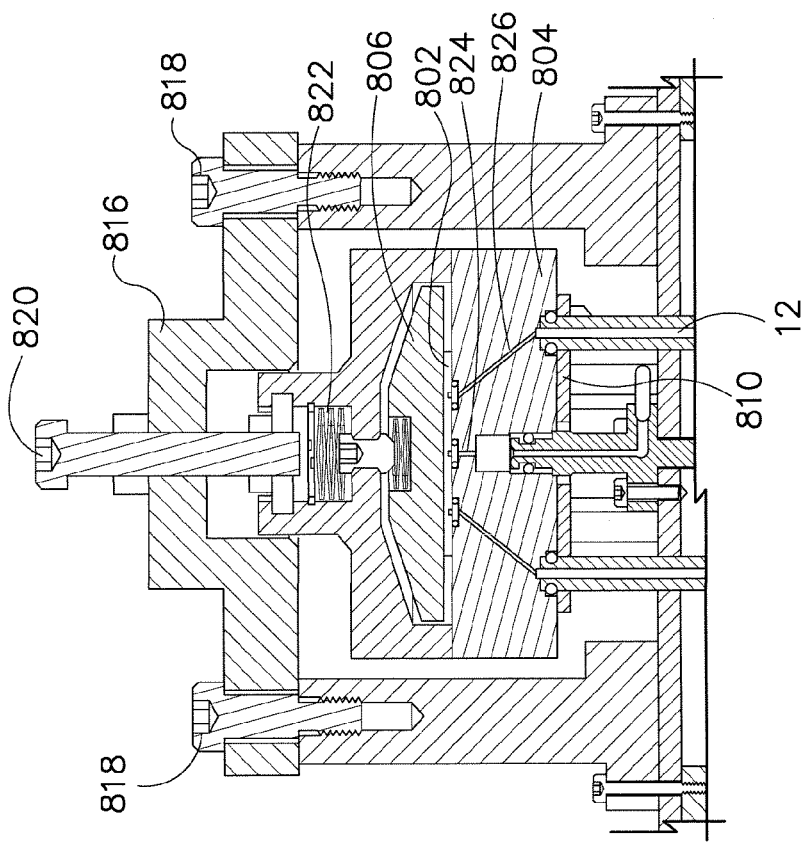
FIG. 8D is a side cross-sectional view of the assembled flow chip assembly of FIG. 8A interfaced with the reactor module.

FIGS. 8E and 8F show perspective views of a bottom plate sealing assembly 830 for the reactor vessels 12. The bottom plate sealing assembly comprises a support plate 832 having O-ring seals 834 corresponding with and seal the outlet of each reactor vessel 12. The bottom seal plate assembly 830 has multiple independent fittings for receiving a common fitting connecting device (not shown) and multiple corresponding independent fitting connecting devices (e.g., ferrule and nut assembly) for connection to outlet lines for delivering the streams to the selection valve.

FIGS. 9A and 9B show cross-sectional side views of the portion of the reactor assembly including the selection valve 408. The selection valve 408 is fed by reactor vessel outlet lines 900 which feed the outlet streams from the reactor vessels 12 to the selection valve 408. In one embodiment, the outlet lines 900 and constructed of nickel-200 tubing, and the selection valve 408 is a 16-port Valco selection valve body and rotor. Designing the reactor system so that the selection valve 408 is inside the pressure chamber 24 allows the use of a standard valve since the pressure differential between the chamber and the flow stream will be small. The selection valve 408 sits on a support 902 which is configured to support the selection valve 408 and accommodate a drive shaft for operating the selection valve 408. The support 902 seals at the interface with the housing via a standard O-ring 904. Pressure in the chamber 24 reinforces the sealing force. The drive shaft is sealed via a spring energized PTFE lip seal 906.

FIGS. 13A and 13B illustrate an alternative embodiment of a selection valve that can be used in the reactor systems described herein, or in other applications requiring the sealing of fluid valves for operation at high pressures and temperatures. In such applications, as discussed above, the high pressure differential between the sealed fluid and the surrounding atmosphere results in high contact loads at seal surfaces. This limits the use of moving parts in such valves that would be required to direct the fluid to various ports, making it difficult to produce and maintain selection valves for such environments.

The valve assembly 1300 shown in FIGS. 13A and 13B addresses this problem by enclosing the mating parts of a valve within a secondary pressure chamber that is controlled to within a small differential pressure of the sealed fluid pressure. In particular, a rotary selection valve 1305 includes a valve body 1310 having multiple input and output ports 1315, with a rotor 1317 seated in an internal cavity formed in valve body 1310, held in place by a cap 1318. Rotor 1317 is coupled through a drive coupling 1320 and rotor drive shaft 1325 to a motor 1330. In the embodiment shown, rotor 1317 is a cone rotor, although other types of rotors, such as flat plate rotors can be used.

A first pressure chamber 1335 is formed at the rotor coupling end of the valve by means of a static seal 1340 and rotor drive shaft seal 1345 held within support (e.g., base member) 1350, while a second pressure chamber 1355 is formed at the opposite end of the valve by means of an upper seal 1360 held within cover housing 1365. The two pressure chambers 1335, 1355 are connected by means of ports 1370, 1375 at a common pressure that is equal to or slightly above or below the sealed gas pressure.

By enclosing only the mating parts of the valve within the pressure chamber(s), this configuration minimizes the pressure differential experienced by these parts while providing for easier service access to valve fittings, reduced pressure chamber volume (which can have safety advantages), reduced manufacturing cost, and the ability to use existing low-pressure sealing technology. In the embodiment shown in FIGS. 13A and 13B, the valve assembly 1300 is constructed using a commercially available multiposition valve (Valco Instruments Co.), although other commercially available or custom designed valves could be used.

Figure 10:
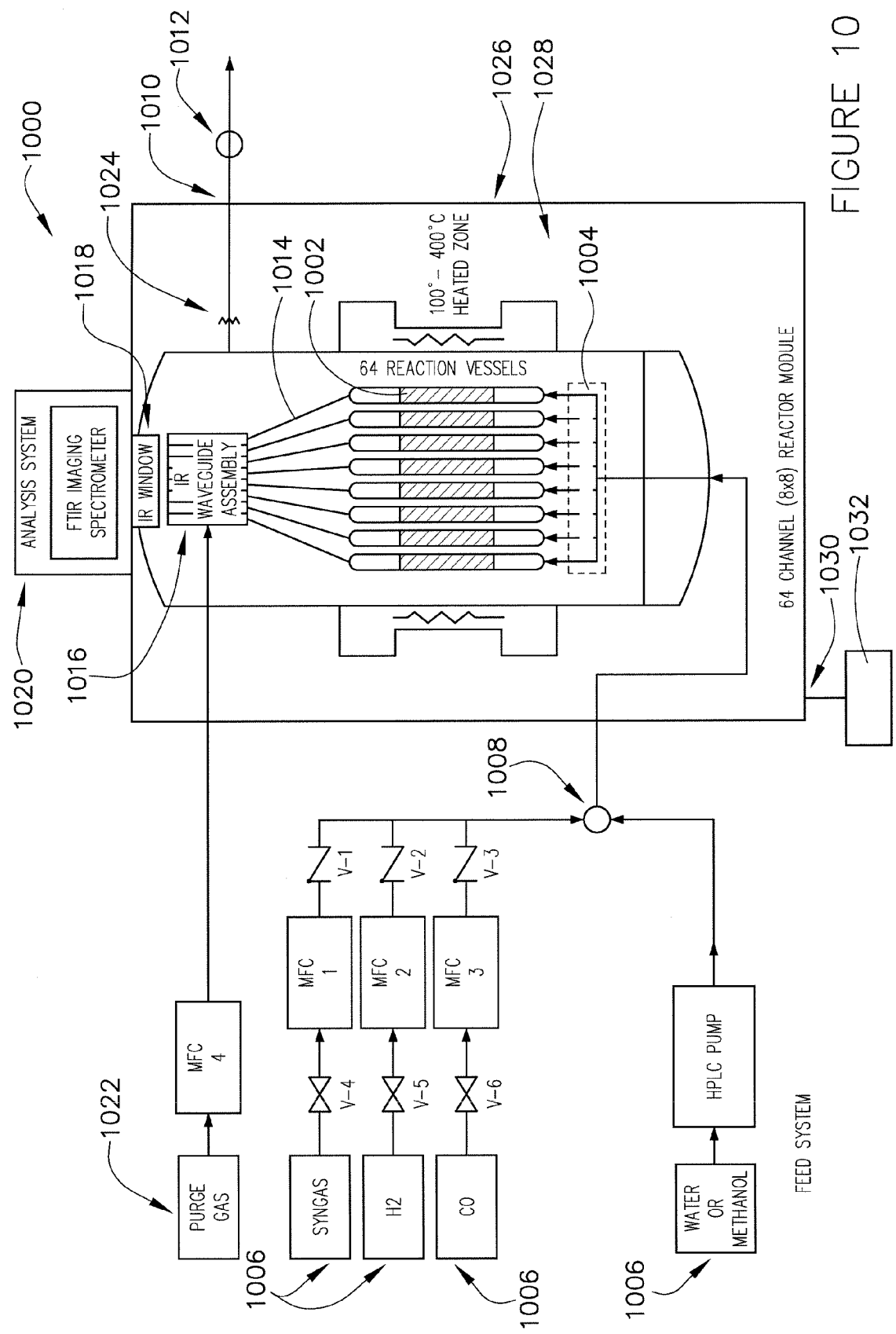
FIG. 10 is a schematic drawing of one embodiment of an apparatus for rapidly screening members of a combinatorial library.

FIG. 10 schematically illustrates another embodiment of the present invention. The specifics of the reactor and analysis are disclosed in U.S. patent application Ser. No. 10/900,612 "Parallel Infrared Spectroscopy Apparatus and Method", which is herein incorporated by reference, which teaches a parallel flow reactor system that utilizes spectroscopic techniques, particularly infrared spectroscopic techniques to screen arrays of materials. The reactor taught therein is a multi-channel fixed bed reactor that does not utilize a selection valve.

The screening apparatus 1000 is comprised of a plurality of vessels 1002 for receiving members of the combinatorial library. Each of the vessels 1002 is in fluid communication with a flow splitting device 1004 (such as a microfluidic fluid distribution manifold), which is in fluid communication with one or more reactant reservoirs 1006 respectively, optionally via a manifold 1008 in embodiments where multiple fluid sources are combined. The vessels 1002 are also in fluid communication with an exit control volume 1010, which controls pressure in the vessels 1102 via a back pressure controller 1012 through outlet conduits 1014, respectively. The number of reactor vessels 1002 is not critical, and is specifically at least four vessels, more specifically at least eight vessels, more specifically at least twelve vessels, more specifically at least sixteen vessels, more specifically at least twenty four vessels, more specifically at least thirty six vessels, more specifically at least forty eight vessels, and even more specifically at least sixty four vessels.

Members of a combinatorial library are screened by simultaneously contacting a subset of library members with nearly equal amounts of test fluid. The test fluid is prepared by combining fluid streams from fluid sources 1006 in a combining manifold 1008, which is in fluid communication with the flow splitting device 1004 and the vessels 1002. During screening, the test fluid flows through the flow splitting device 1004 (such as a flow splitting chip, such as a 64 channel flow splitter taught in PCT Application No. WO 00/51720, which splits the incoming feed stream and flows the test fluid through up to 64 reactor vessels) and through each of the vessels 1102.

After exiting the reaction chambers, the fluids from the reactors are respectively provided to the detection system which comprises a waveguide assembly 1016, an IR transparent window 1018 and an IR spectrometer 1020, preferably an FTIR spectrometer. The samples can be analyzed sequentially or in parallel by the detection device. A purge gas 1022 enters the waveguide assembly 1018 and combines with the exiting fluids. After analysis, the fluids are combined and exit the system through an outlet channel 1024 to the exit control volume.

A housing 1026 encloses the vessels 1002 and preferably the flow splitting device 1016 and waveguide assembly 1018, providing a chamber 1028 that can be pressurized to high pressures, allowing reactions in the vessels 1002 to occur at high pressures while applying a low pressure differential on the reactor components in the chamber, such as coupling, fittings and valves. The housing 1026 includes an inlet port 1030 for pressurizing the pressure chamber 1028 from an external pressure source 1032. The housing 1026 also comprises the IR-transparent window 1018 so that the detector can analyze the fluids in the waveguide assembly 1018.

Figure 11:
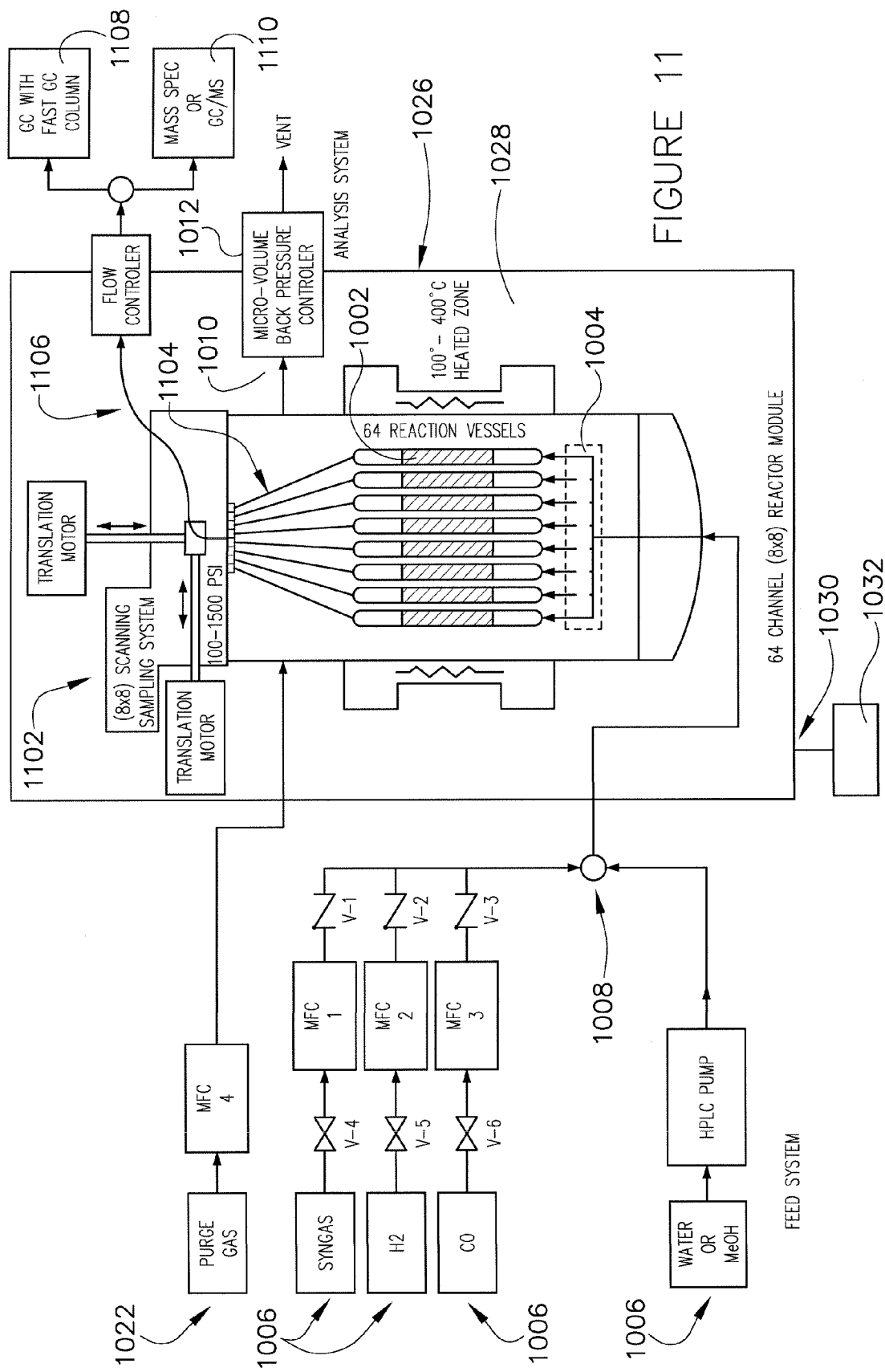
FIG. 11 is a schematic drawing of one embodiment of an apparatus for rapidly screening members of a combinatorial library.

FIG. 11 schematically illustrates another embodiment of the present invention. The embodiment of FIG. 11 utilizes a 3-axis scanning probe 1102 to sequentially sample fluids in the outlet channels 1104 of the reactor and send the fluids to a detector, such as a gas chromatograph 1108 or a mass spectrometer 1110, through a sample bypass 1106. The remaining streams are combined and exit the system to an exit control volume which controls pressure in the system via a back pressure controller.

Figure 12:
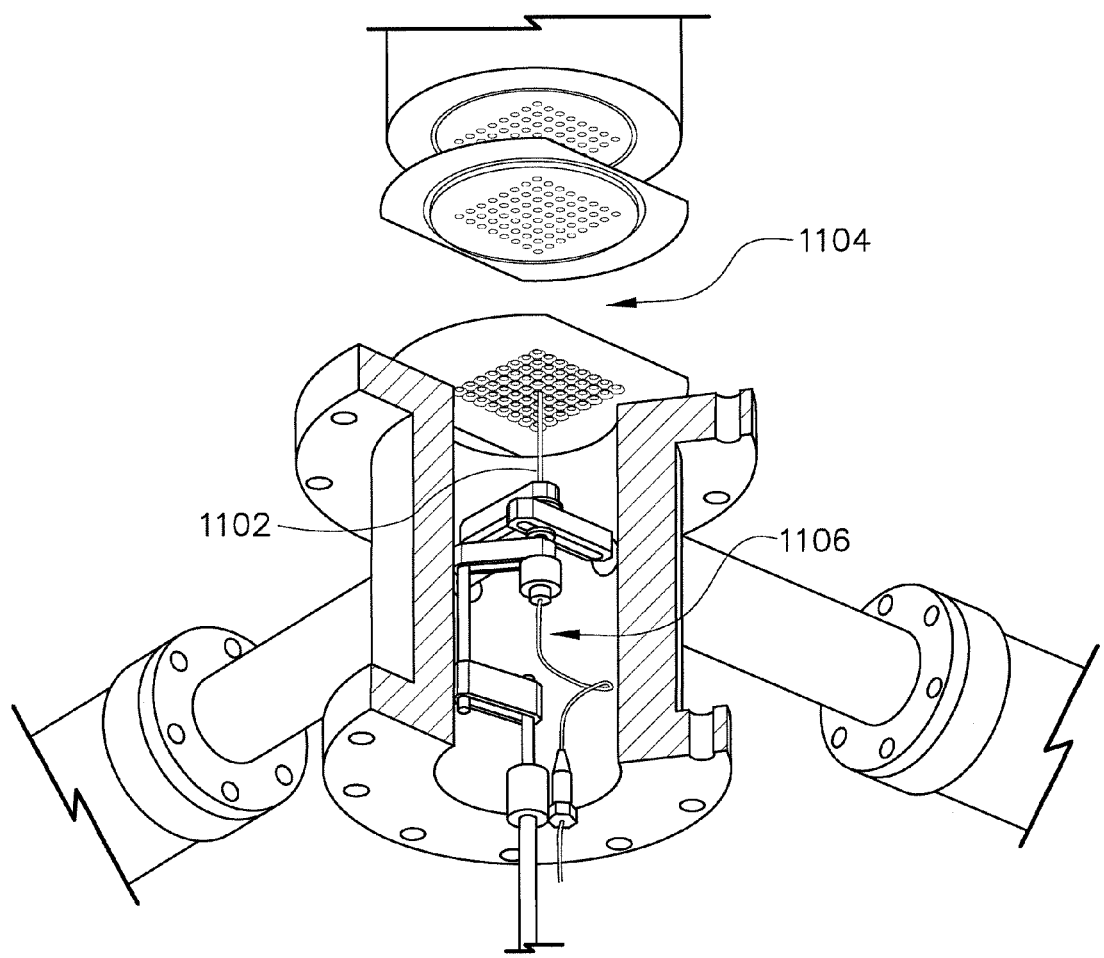
FIG. 12 is a perspective view of an exemplary 3-axis sampling probe as described in FIG. 11.

A perspective view of the 3-axis sampling probe is shown in FIG. 12.

The accompanying Figures and this description depict and describe embodiments of the reactor system and method of the present invention, and features and components thereof. Fastening, mounting, attaching or connecting the components of the present invention to form the apparatus or device as a whole, unless specifically described otherwise, are intended to encompass conventional fasteners such as machine screws, nut and bolt connectors, machine threaded connectors, snap rings, clamps such as screw clamps and the like, rivets, nuts and bolts, toggles, pins and the like. Components may also be connected by welding, friction fitting or deformation, if appropriate. Unless specifically otherwise disclosed or taught, materials for making components of the present invention are selected from appropriate materials such as metal, metallic alloys, fibers, plastics and the like, and appropriate manufacturing or production methods including casting, extruding, coating, molding and machining may be used.

Any references herein to front and back, right and left, top and bottom, upper and lower and horizontal and vertical are intended for convenience of description only, not to limit the present invention or its components to any one positional or spatial orientation. Such terms are to be read and understood with their conventional meanings. In the Figures, elements common to the embodiments of the invention are commonly identified.

It is contemplated that various changes may be made without deviating from the spirit and scope of the present invention. Accordingly, it is intended that the scope of the present invention not be limited strictly to that of the above description of the present invention.

In light of the detailed description of the invention and the examples presented above, it can be appreciated that the several objects of the invention are achieved.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

We claim:

1. A method of screening a plurality of materials, the method comprising:
    confining the plurality of materials in a plurality of vessels, each material of the plurality of materials being confined in a separate vessel of the plurality of vessels;
    enclosing the plurality of vessels in a chamber,
        the chamber further enclosing a flow splitting device;
    supplying a gas into the chamber to pressurize the chamber to a first pressure above an atmospheric pressure,
        wherein the flow splitting device and each of the plurality of vessels are subjected to the first pressure;
    contacting each of the plurality of materials with a test fluid by flowing the test fluid from the flow splitting device and into each of the vessels under reaction conditions comprising a second pressure above the atmospheric pressure in each of the vessels during the contacting step, the second pressure being different from the first pressure,
        the test fluid being different from the gas used to pressurize the chamber;
    detecting changes in the test fluid following contact with each of the plurality of materials; and
    relating changes in the test fluid to a property of each of the plurality of materials.

2. The method of claim 1, wherein the plurality of vessels comprises at least four vessels.

3. The method of claim 1, wherein the plurality of vessels comprises at least sixteen vessels.

4. The method of claim 1, wherein the detecting step comprises detecting changes with an infrared spectrometer.

5. The method of claim 1, wherein the detecting step comprises detecting changes with an FTIR spectrometer.

6. The method of claim 1, wherein the detecting step comprises detecting changes with a mass spectrometer.

7. The method of claim 1, wherein the first pressure is greater than 50 psi.

8. The method of claim 1, wherein the first pressure is greater than 200 psi.

9. The method of claim 1, wherein the first pressure is greater than 1000 psi.

10. The method of claim 1, wherein a difference between the first pressure in the chamber and the second pressure in the vessels during the contacting step is less than 200 psi.

11. The method of claim 1, wherein a difference between the first pressure in the chamber and the second pressure in the vessels during the contacting step is less than 50 psi.

12. The method of claim 1, wherein the reaction conditions further comprise a temperature greater than 100° C.

13. The method of claim 1, wherein the reaction conditions further comprise a temperature greater than 300° C.

14. The method of claim 1, wherein the detecting step comprises detecting changes in the test fluid using at least one of gas chromatography, mass spectroscopy, visible spectroscopy, ultraviolet spectroscopy, and infrared spectroscopy.

15. The method of claim 1, wherein the property is a catalytic property of each of the plurality of materials.

16. The method of claim 1, wherein the chamber further encloses an exit volume control comprising a sample bypass and one or more outlet conduits.

17. The method of claim 1, wherein a difference between the second pressure and the first pressure is less than a difference between the first pressure and the atmosphere.

18. The method of claim 1, wherein the flow splitting device is a microfluidic distribution manifold.

19. The method of claim 1, wherein each of the plurality of vessels receives a same amount of the test fluid.

20. The method of claim 1, wherein the detecting changes in the test fluid comprises flowing the test fluid into a detector, the detector being positioned outside of the chamber and exposed to the atmospheric pressure.

21. The method of claim 1, wherein the contacting each of the plurality of materials with the test fluid comprises flowing the test fluid from a manifold connected to one or more reactant reservoirs, the manifold and the one or more reactant reservoirs being positioned outside of the chamber and exposed to the atmospheric pressure.

22. The method of claim 1, wherein the chamber comprises an inlet port for pressurizing the chamber to the first pressure, the inlet port being connected to an external pressure source.

23. The method of claim 1, further comprising maintaining a pressure differential between the first pressure and the second pressure within a predetermined range using a pressure controller.

24. The method of claim 23, wherein the first pressure is automatically adjusted based on changes to the second pressure in order to maintain the pressure differential within predetermined range.

25. The method of claim 23, wherein the pressure differential is maintained within predetermined range during supplying the gas into the chamber to pressurize the chamber to the first pressure.

26. The method of claim 23, wherein the pressure differential is maintained within predetermined range at all times.

27. The method of claim 1, wherein the chamber comprises a base, a cover, and one or more fasteners for connecting the base and the cover and for maintaining the first pressure within the chamber.

28. The method of claim 1, wherein the chamber comprises one of 17-4PH/H1100 stainless steel, 17-4PH/H1150 stainless steel, and 6AI-4V titanium.

\* \* \* \* \*